United States Patent
Nakano

(10) Patent No.: US 8,546,546 B2
(45) Date of Patent: Oct. 1, 2013

(54) ANTI-MUC 17 ANTIBODY

(75) Inventor: Kiyotaka Nakano, Tokyo (JP)

(73) Assignee: Forerunner Pharma Research Co., Ltd., Tokyo (JP)

(*) Notice: Subject to any disclaimer, the term of this patent is extended or adjusted under 35 U.S.C. 154(b) by 182 days.

(21) Appl. No.: 12/667,595

(22) PCT Filed: Jul. 3, 2008

(86) PCT No.: PCT/JP2008/001777
§ 371 (c)(1),
(2), (4) Date: May 5, 2010

(87) PCT Pub. No.: WO2009/004822
PCT Pub. Date: Jan. 8, 2009

(65) Prior Publication Data
US 2010/0240872 A1 Sep. 23, 2010

(30) Foreign Application Priority Data

Jul. 4, 2007 (JP) ................................ 2007-176319

(51) Int. Cl.
| | |
|---|---|
| C07K 1/00 | (2006.01) |
| C07K 14/00 | (2006.01) |
| C07K 16/00 | (2006.01) |
| C07K 17/00 | (2006.01) |
| A61K 35/14 | (2006.01) |
| A61K 38/16 | (2006.01) |
| C12P 21/08 | (2006.01) |

(52) U.S. Cl.
USPC ...... 530/388.85; 530/350; 530/380; 530/385; 530/386; 530/387.1; 530/387.3; 530/387.7; 530/387.9; 530/388.1; 530/388.15; 530/388.8

(58) Field of Classification Search
None
See application file for complete search history.

(56) References Cited

U.S. PATENT DOCUMENTS 7,078,188 B2 * 7/2006 Batra et al. ................. 435/69.1
2005/0100925 A1    5/2005 Batra et al.

FOREIGN PATENT DOCUMENTS

| EP | 1 176 195 A1 | 1/2002 |
| WO | 00-61739 A1 | 10/2000 |

OTHER PUBLICATIONS

Extended European Search Report for Appl. No. 08790149.2 dated Jul. 6, 2010.
Malmberg, Emily K., et al. "Increased Levels of mucins in the cystic fibrosis mouse small intestine, and modulator effects of the Muc1 mucin expression", American Journal of Physiology-Gastrointestinal and Liver Physiology, Aug. 2006, pp. G203-G210, vol. 291, No. 2.
Malmberg, Emily K., et al. "The C-Terminus of the transmembrane mucin MUC17 binds to the scaffold protein PDZK1 that stably localizes it to the enterocyte apical membrane in the small intestine", Biochemical Journal, Nov. 8, 2007, pp. 283-289, vol. 410, No. Part 2.
International Search Report for PCT/JP2008/001777; Aug. 6, 2008.
N. Moniaux et al., "Characterization of Human Mucin MUC17", J Biol Chem, 281(33), p. 23676-23685, Jan. 11, 2006.
Ho Jenny J L et al., "N-glycosylation is required for the surface localization of MUC17 mucin", In: International Journal of Oncology, 23(3), p. 585-592, Sep. 2003, BIOSIS Accession No. 2003:421452.
JR Gum et al., "MUC17, a Novel membrane-tethered mucin", In: Biochem Biphys Res Commun, 291, p. 466-475, Jan. 15, 2002.

* cited by examiner

*Primary Examiner* — Alana Harris Dent
(74) *Attorney, Agent, or Firm* — Sughrue Mion, PLLC

(57) ABSTRACT

An antibody that binds to Mucin17 (Muc17) is disclosed. The antibody of the present invention preferably binds to the peptide of SEQ ID NO:3 and does not bind to the peptide of SEQ ID NO:4 or the peptide of SEQ ID NO:5. Also disclosed are an anti-cancer agent, preferably an anti-cancer agent for pancreatic cancer, which comprises the antibody of the present invention, as well as a method of diagnosing cancer using the antibody of the present invention, preferably the antibody of the present invention that does not bind to the secreted-form of Muc17.

5 Claims, 3 Drawing Sheets

ANTI-MUC 17 ANTIBODY

RELATED APPLICATION

This application claims priority based on the Japanese Patent Application No. 2007-176319 filed 4 Jul. 2007, the contents of which are hereby incorporated by reference.

TECHNICAL FIELD

1. Technical Field

The present invention relates to an anti-cancer agent, as well as a method of diagnosing cancer.

2. Background Art

Mucin 17 (Muc17) is a newly found mucin that belongs to the membrane-bound mucin family. Its expression in normal tissue is limited to the small intestine and large intestine (J. R. Gum, Jr., S. C. Crawley, J. W. Hicks, D. E. Szymkowski, and Y. S. Kim, MUC17, a novel membrane-tethered mucin. Biochem. Biophys. Res. Commun., 291 (2002) 466-75). The most part of the extracellular domain comprises a tandem repeat of serine-, threonine-, and proline-rich 59-mer consensus sequence. It is believed to be involved in cytoprotection through a glycosylated mucin structure. An extracellular SEA domain is also present, which implies the existence of a secreted-form of Muc17 generated by cleavage (J. R. Gum, et al, supra). Moreover, the existence of a secreted-form of Muc17 lacking the transmembrane domain has been reported as a splicing variant (N. Moniaux, W. M. Junker, A. P. Singh, A. M. Jones, and S. K. Batra, Characterization of human mucin MUC17. Complete coding sequence and organization. J. Biol. Chem., 281 (2006) 23676-85).

With regard to expression in cancers, expression of the Muc17 gene at RNA level has been observed in the AsPc-1 pancreatic cancer cell line and in the NCI-H498, Caco-2, and LS174T colon cancer cell lines. In addition, the expression of Muc17 at protein level has been observed by the immunostaining of clinical pancreatic cancer tissue using polyclonal antibodies prepared against Pro-Thr-Thr-Ala-Glu-Gly-Thr-Ser-Met-Pro-Thr-Ser-Thr-Pro-Ser-Glu (SEQ ID NO:38), which corresponds to the tandem repeat sequence (N. Moniaux, et al., supra).

The references cited herein are provided below. The contents of these documents are hereby incorporated by reference in its entirety. None of these documents are admitted to constitute a prior art of the present invention.

[Non-patent Reference 1] J. R. Gum, Jr., S. C. Crawley, J. W. Hicks, D. E. Szymkowski, and Y. S. Kim, MUC17, a novel membrane-tethered mucin. Biochem. Biophys. Res. Commun., 291 (2002) 466-75.

[Non-patent Reference 2] N. Moniaux, W. M. Junker, A. P. Singh, A. M. Jones, and S. K. Batra, Characterization of human mucin MUC17. Complete coding sequence and organization. J. Biol. Chem., 281 (2006) 23676-85.

DISCLOSURE OF THE INVENTION

An object of the present invention is to provide a novel antibody and an anti-cancer agent comprising the same, as well as a method of diagnosing cancer using the same.

The inventors obtained a monoclonal antibody against the extracellular juxtamembrane region of Mucin 17 (Muc17) and discovered that the antibody exhibits ADCC activity, and also exhibits an anti-tumor activity upon conjugated with a toxin.

The present invention provides an antibody that binds to Muc17. The antibody of the present invention preferably does not bind to a secreted-form of Muc17. Also preferably the antibody of the present invention binds to the peptide of SEQ ID NO:3 (4176-4390), but does not bind to the peptide of SEQ ID NO:4 (4244-4390) or the peptide of SEQ ID NO:5 (4115-4243).

In a preferred embodiment, the antibody of the present invention exhibits ADCC activity. Also preferably the antibody of the present invention is a chimeric antibody or a humanized antibody. Also preferably the antibody of the present invention is a low-fucosylated antibody.

In another preferred embodiment, the antibody of the present invention recognizes an epitope that is the same as the epitope recognized by the antibody (MQ155) that has a heavy chain variable region having the amino acid sequence set forth in SEQ ID NO:23 and a light chain variable region having the amino acid sequence set forth in SEQ ID NO:25.

The present invention also provides an anti-cancer agent comprising the antibody of the present invention, preferably an anti-cancer agent against pancreatic cancer. The invention further provides a method of diagnosing cancer using the antibody of the present invention. Preferably the antibody that does not bind to the secreted-form of Muc17.

PREFERRED EMBODIMENTS OF THE INVENTION

Muc17

Figure 1:
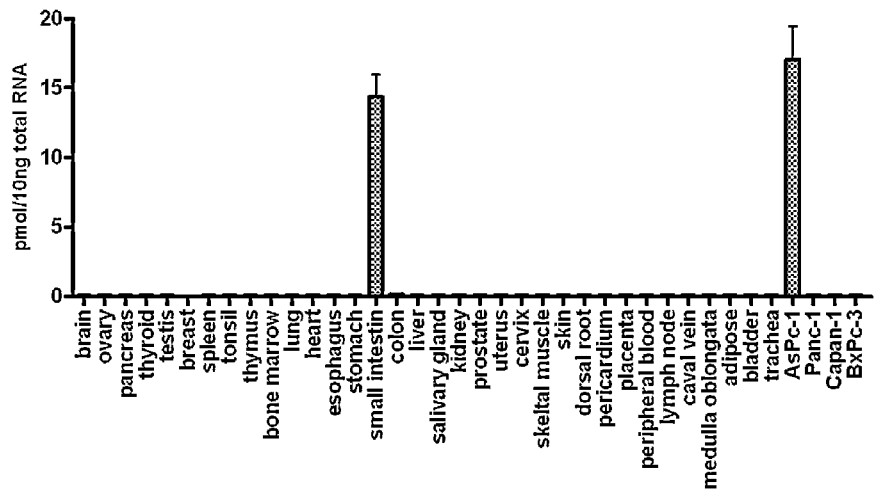
FIG. 1 shows the amount of Muc17 mRNA in normal tissue and in cancer cell lines.

Mucin 17 (Muc17; Accession No. NM_001040105) is a type 1 membrane protein comprising 4,493 amino acids. The nucleotide sequence encoding Muc17 is shown in SEQ ID NO:1 and the amino acid sequence of Muc17 is shown in SEQ ID NO:2. Muc17 belongs to the membrane-form mucin family, and most part of its extracellular domain comprises a tandem repeat of a serine-, threonine-, and proline-rich 59-mer sequence and is glycosylated. In addition, it comprises an SEA domain (4182Glu-4287Asn), suggesting that the protein is cleaved and that at least a part of the protein may be present in the secreted form. The existence of the secreted-form splicing variant (same sequence in 1Met-4241Arg) has also been reported (N. Moniaux, et al., supra).

Anti-Muc17 Antibody

The source (mouse, rat, human, and so forth), type (monoclonal antibody, polyclonal antibody), configuration (altered antibody, low molecular weight antibody, modified antibody, and so forth), and so forth of the anti-Muc17 antibody of the present invention are not critical as long as the antibody binds to Muc17.

Preferably the anti-Muc17 antibody of the present invention specifically binds to Muc17. The anti-Muc17 antibody of the present invention is also preferably a monoclonal antibody.

The anti-Muc17 antibody of the present invention preferably recognizes and binds to the extracellular domain of the Muc17 protein. The extracellular domain of the Muc17 protein corresponds to positions 1 to 4389 in the amino acid sequence set forth in SEQ ID NO:2. More preferably, the anti-Muc17 antibody of the present invention binds to the extracellular domain of the Muc17 protein but does not bind to the secreted-form of Muc17. The secreted-form of Muc17 corresponds to positions 1 to 4241 in the amino acid sequence set forth in SEQ ID NO:2.

In a preferred embodiment of the present invention, the anti-Muc17 antibody is an antibody that binds to the peptide comprising the amino acid sequence of SEQ ID NO:3 (4176-4390) and does not bind to the peptide comprising the amino acid sequence of SEQ ID NO:4 (4244-4390) and does not bind to the peptide comprising the amino acid sequence of SEQ ID NO:5 (4115-4243).

One can determine whether an antibody binds to a particular peptide by known procedures (Antibodies: A Laboratory Manual. Edited by Ed Harlow and David Lane, Cold Spring Harbor Laboratory, 1988). For example, enzyme-linked immunosorbent assay (ELISA), enzyme immunoassay (EIA), radioimmunoassay (RIA), immunofluorescent methods, and so forth can be used. More specifically, one can determine whether an antibody binds to a particular peptide by the methods described in the examples provided below.

The following antibodies are specific examples of the anti-Muc17 antibody of the present invention:

(1) an antibody (MQ128) that comprises a heavy chain variable region that has CDR1 comprising the amino acid sequence set forth in SEQ ID NO:6, CDR2 comprising the amino acid sequence set forth in SEQ ID NO:7, and CDR3 comprising the amino acid sequence set forth in SEQ ID NO:8;
(2) an antibody that comprises a light chain variable region that has CDR1 comprising the amino acid sequence set forth in SEQ ID NO:9, CDR2 comprising the amino acid sequence set forth in SEQ ID NO:10, and CDR3 comprising the amino acid sequence set forth in SEQ ID NO:11;
(3) an antibody that comprises the heavy chain variable region of (1) and the light chain variable region of (2);
(4) an antibody that comprises a heavy chain variable region comprising the amino acid sequence set forth in SEQ ID NO:19;
(5) an antibody that comprises a light chain variable region comprising the amino acid sequence set forth in SEQ ID NO:21;
(6) an antibody that comprises the heavy chain variable region of (4) and the light chain variable region of (5);
(7) an antibody (MQ155) that comprises a heavy chain variable region that has CDR1 comprising the amino acid sequence set forth in SEQ ID NO:12, CDR2 comprising the amino acid sequence set forth in SEQ ID NO:13, and CDR3 comprising the amino acid sequence set forth in SEQ ID NO:14;
(8) an antibody that comprises a light chain variable region that has CDR1 comprising the amino acid sequence set forth in SEQ ID NO:15, CDR2 comprising the amino acid sequence set forth in SEQ ID NO:16, and CDR3 comprising the amino acid sequence set forth in SEQ ID NO:17;
(9) an antibody that comprises the heavy chain variable region of (7) and the light chain variable region of (8);
(10) an antibody that comprises a heavy chain variable region comprising the amino acid sequence set forth in SEQ ID NO:23;
(11) an antibody that comprises a light chain variable region comprising the amino acid sequence set forth in SEQ ID NO:25;
(12) an antibody that comprises the heavy chain variable region of (10) and the light chain variable region of (11); and
(13) an antibody that recognizes an epitope that is the same epitope recognized by any of the antibodies given in (1) to (12).

One can determine whether a test antibody has a common epitope with a certain antibody by detecting the competition of the two antibodies for the same epitope. Competition between antibodies can be detected by, for example, a cross-blocking assay. For example, a competitive ELISA assay is a preferred cross-blocking assay. Specifically, in a cross-blocking assay, Muc17 protein coated on the wells of a microtiter plate is pre-incubated in the presence of a candidate competitive antibody or in the absence of the antibody, and the anti-Muc17 antibody of the present invention is added. The quantity of anti-Muc17 antibody of the present invention that binds to the Muc17 protein in the wells will indirectly relate to the binding capacity of the candidate competitive antibody (test antibody) that competes for binding to the same epitope. Thus, when the test antibody has a larger affinity for the same epitope, a lower amount of the anti-Muc17 antibody of the present invention and a larger amount of the test antibody will bind to the Muc17 protein coated on the wells.

The amount of antibody bound to the wells can be readily measured by means of a label preliminary attached to the antibody. For example, a biotin-labeled antibody can be assayed using an avidin-peroxidase conjugate and a suitable substrate. The term "competitive ELISA assay" is applied in particular to a cross-blocking assay that employs an enzyme label such as a peroxidase. The antibody can be labeled with any other labels that allow for detection or measurement. In specific terms, radiolabels and fluorescent labels are known in this regard.

In addition, when the test antibody has a constant region that originates in a species different from that of the anti-Muc17 antibody of the present invention, the amount of antibody bound to the wells may also be measured by a labeled antibody that recognizes the constant region of that antibody. Alternatively, when the test antibody originates in the same species but different classes, the amount of antibody bound to the wells can be measured with an antibody that discriminates among the classes.

If a candidate competitive anti-Muc17 antibody can block the binding of the anti-Muc17 antibody of the invention at least by 20%, preferably at least by 20 to 50%, and more preferably at least by 50% compared to the binding activity obtained in a control test carried out in the absence of the candidate competitive antibody, the candidate antibody is an antibody that binds to substantially the same epitope as the anti-Muc17 antibody of the present invention or that competes for binding to the same epitope.

For the purposes of the present invention, an epitope may be any epitope, for example, a three-dimensional epitope or a linear epitope.

Cytotoxic Activity

An antibody that exhibits cytotoxic activity is an example of a preferred embodiment of the antibody of the present invention. For the purposes of the present invention, the cytotoxic activity includes, for example, antibody-dependent cell-mediated cytotoxicity (ADCC) and complement-dependent cytotoxicity (CDC). As used herein, the CDC activity refers to a cell-killing activity through the complement system. The ADCC activity, on the other hand, refers to an activity in which a specific antibody binds to a cell surface antigen on a target cell, then an Fcγ receptor-presenting cell (e.g., an immune cell) binds through its Fcγ receptor to the Fc region of the antigen-bound antibody, and attacks the target cell.

Known methods can be used to measure whether an antibody exhibits ADCC activity or whether an antibody exhibits CDC activity (for example, Current Protocols in Immunology. Chapter 7: Immunologic Studies in Humans. Editor: John E. Coligan et al., John Wiley & Sons, Inc. (1993), and so forth).

In specific terms, effector cells, a complement solution, and target cells are first prepared.

(1) Preparation of Effector Cells

The spleen is removed from, for example, CBA/N mice, and the splenocytes are separated in RPMI1640 medium (Invitrogen Corporation). After washing the cells with the same medium containing 10% fetal bovine serum (FBS, HyClone), the effector cells can be prepared by adjusting the cell concentration to $5 \times 10^6$/mL.

(2) Preparation of Complement Solution

The complement solution can be prepared by the 10-fold dilution of baby rabbit complement (Cedarlane Laboratories Ltd.) with medium containing 10% FBS (Invitrogen Corporation).

(3) Preparation of the Target Cells

Cells that express Muc17 protein are cultured with 0.2 mCi $^{51}$Cr sodium chromate (GE Healthcare Biosciences) for 1 hour at 37° C. on DMEM medium containing 10% FBS in order to radiolabel the target cells. Muc17 expressing cells may include, for example, cancer cells (e.g., pancreatic cancer cells and colon cancer cells) or cells transformed with a Muc17 protein-encoding gene. After radiolabeling, the cells are washed 3 times with RPMI1640 medium containing 10% FBS and the target cells are prepared by adjusting the cell concentration to $2 \times 10^5$/mL.

The ADCC activity and CDC activity can be measured by the following methods. In order to measure the ADCC activity, 50 μL target cells and 50 μL anti-Muc17 antibody are added to a 96-well U-bottom plate (Becton, Dickinson and Company) and a reaction is carried out for 15 minutes on ice. Then 100 μL effector cells is added and incubated for 4 hours in a $CO_2$ incubator. A final antibody concentration is 0 or 10 μg/mL. After incubation, 100 μL of the supernatant is taken and the radioactivity is measured with a gamma counter (COBRA II AUTO-GAMMA, MODEL D5005, Packard Instrument Company). The cytotoxic activity (%) can be calculated from the equation:

$$(A-C)/(B-C) \times 100$$

where A is the radioactivity (cpm) in the particular sample, B is the radioactivity (cpm) in a sample to which 1% NP-40 (Nacalai Tesque, Inc.) has been added, and C is the radioactivity (cpm) of a sample containing only the target cells.

To measure the CDC activity 50 μL target cells and 50 μL anti-Muc17 antibody are added to a 96-well flat-bottom plate (Becton, Dickinson and Company) and a reaction is carried out for 15 minutes on ice. Then 100 μL complement is added and incubated for 4 hours in a $CO_2$ incubator. A final antibody concentration is 0 or 3 μg/mL. After incubation, 100 μL supernatant is taken and the radioactivity is measured with a gamma counter. The cytotoxic activity can be calculated in the same manner as for measurement of the ADCC activity.

Sugar Chain-Modified Antibodies

Antibody having a modified sugar chain is another preferred embodiment of the antibody of the present invention. It is known that the cytotoxic activity exhibited by an antibody can be enhanced by modification of the sugar chains on the antibody.

The following are examples of sugar chain-modified antibodies: antibodies that have an altered glycosylation pattern (for example, WO 99/54342), antibodies in which fucose on the sugar chain has been removed (for example, WO 00/61739, WO 02/31140, WO 2006/067847, and WO 2006/067913), and antibodies that have a sugar chain containing a bisecting GlcNAc (for example, WO 02/79255).

A fucose-deficient antibody is an example of a preferred sugar chain-modified antibody of the present invention. The sugar chains attached to antibodies include N-glycosyl linked sugar chain which is attached to the nitrogen atom on the side chain of asparagine in the antibody molecule, and O-glycosyl linked sugar chain which is attached to the hydroxyl group on the side chain of serine or threonine in the antibody molecule. In the present invention, the presence/absence of fucose is related to N-glycosyl linked sugar chains.

For the purposes of the present invention, a fucose-deficient antibody denotes an antibody which lacks fucose on at least 20%, preferably at least 50%, more preferably at least 70%, and even more preferably at least 90% of the N-glycosyl linked sugar chains.

Fucose-deficient antibodies can be constructed by methods known to those skilled in the art. In order to produce a fucose-deficient antibody, for example, an antibody is expressed in a host cell that has either no capacity or a reduced capacity to attach α-1,6 core fucose. There are no particular limitations on the host cell that has either no capacity or a reduced capacity to attach fucose, and examples of such a host cell include rat myeloma YB2/3HL.P2.G11.16Ag.20 cells (known as YB2/0 cells, stored under ATCC CRL 1662), FTVIII knock-out CHO cells (WO 02/31140), Lec13 cells (WO 03/035835), and fucose transporter-negative cells (WO 2006/067847, WO 2006/067913).

Sugar chain may be analyzed by methods known to those skilled in the art. For example, the sugar chain is released from the antibody by the action of N-glycosidase F (Roche). The sugar chain preparation is desalted by solid-phase extraction using a cellulose cartridge (Shimizu Y. et al., Carbohydrate Research, 332 (2001), 381-388), concentrated to dryness and subjected to fluorescence labeling with 2-aminopyridine (Kondo A. et al., Agricultural and Biological Chemistry, 54:8 (1990), 2169-2170). The reagent is then removed from the resulting pyridylaminated sugar chain by solid-phase extraction using a cellulose cartridge, and concentrated by centrifugation to provide a purified pyridylaminated sugar chain. The sugar chain may be analyzed by reverse-phase HPLC using ODS column. Alternatively, the pyridylaminated sugar chain is prepared and subjected to a two-dimensional mapping with a combination of reverse-phase HPLC analysis on ODS column and normal-phase HPLC analysis on an amine-based column.

Chimeric Antibodies and Humanized Antibodies

Chimeric antibodies and humanized antibodies are additional examples of preferred embodiments of the antibody of the present invention. A chimeric antibody refers to an antibody in which regions having different origins are linked to each other. Chimeric antibodies are generally constructed from a constant (C) region originating from a human antibody and a variable (V) region from an antibody originating from a non-human animal. For example, a mouse-human heterologous chimeric antibody comprises heavy chain and light chain variable regions from a mouse antibody and heavy chain and light chain constant regions from a human antibody.

In contrast, a humanized antibody is constructed from the complementarity determining region (CDR) of an antibody originating from a non-human animal and a framework region (FR) originating from a human antibody and a C region originating from a human antibody. Due to its lower antigenicity in the human body, a humanized antibody will be useful as an effective ingredient of the therapeutic agent of the present invention. Humanized antibodies are also called reshaped human antibodies. For example, humanized antibodies are known to have the CDRs from an antibody originating a non-human animal, such as mouse, which is grafted into a human antibody. General gene recombination techniques for obtaining humanized antibodies are known in the art.

In specific terms, for example, overlap extension PCR technique may be used for grafting mouse antibody CDRs into human FRs. In the overlap extension PCR, a nucleotide sequence coding for the mouse antibody CDR to be grafted is attached to a primer for synthesis of a human antibody FR. Primers are prepared for each of the four FRs. In the grafting of mouse CDR to human FR, the selection of human FR that is highly homologous to the mouse FR is generally advantageous for preserving CDR functionality. Thus, it is generally preferred to use human FR comprising an amino acid sequence that is highly homologous with the amino acid sequence of the mouse FR adjacent to the mouse CDR to be grafted.

In addition, the nucleotide sequences of the fragments that are ligated are designed to be joined together in-frame. The human FRs are separately synthesized using the respective primers to obtain products in which DNA encoding mouse CDR is appended to each FR. The nucleotide sequences encoding mouse CDR in the individual products are designed to overlap with each other. Then, the overlapping CDR moieties of the products are annealed with each other and a complementary strand is synthesized using a human antibody gene as the template. By this reaction, the human FRs are joined together via mouse CDR sequences.

In the final step, the V region gene containing 3 CDRs and 4 FRs are amplified using primers which anneals to the 5'- and 3'-ends of the gene and containing suitable restriction enzyme recognition sequences to obtain a full length product. The DNA obtained as above and DNA encoding a human antibody C region are inserted in-flame into an expression vector to construct a human-type antibody expression vector. The recombinant vector is transfected into a host cell to establish a recombinant cell, and the recombinant cell is cultured for expression of the DNA encoding a humanized antibody. The humanized antibody is prepared from the culture medium of the recombinant cells (see EP 239400 and WO 96/02576).

The humanized antibody produced as above is qualitatively or quantitatively analyzed and evaluated for its antigen binding activity to select human antibody FRs that, when connected through CDRs, enable the CDRs to form high-quality antigen binding sites. In addition, amino acid residues in the FRs may be substituted as necessary, so as to enable the CDRs of the reshaped human antibody to form optimal antigen binding sites. For example, amino acid sequence mutations can be introduced into the FRs by modifying the PCR procedure employed to graft the mouse CDRs into the human FRs. Specifically, a partial mutation can be introduced into the nucleotide sequence of the primer to be annealed to FR. A nucleotide sequence mutation is introduced into the FR by synthesizing the FR with the primer. A variant FR sequence having desirable properties can be selected by determining and evaluating the antigen binding capacity of the amino acid-substituted antibody variant using the method described above (Sato, K. et al., Cancer Res., 1993, 53, 851-856).

Bivalent Antibodies, Low Molecular Weight Antibodies, and Modified Antibodies

The anti-Muc17 antibody of the present invention encompasses not only bivalent antibodies such as IgG, but also monovalent antibodies and multivalent antibodies such as IgM insofar as the antibody binds to the Muc17 protein. The multivalent antibodies of the present invention encompass those antibodies in which the antigen binding sites are all the same, and those antibodies in which all or some of the antigen binding sites are different from each other.

The antibody of the present invention is not limited to the full length antibody molecule but may be a low molecular weight antibody or a modified antibody as long as the antibody is capable of binding to the Muc17 protein.

Low molecular weight antibody encompasses antibody fragments generated by the deletion of a portion of the whole antibody (for example, whole IgG). A partial deletion of the antibody molecule is permissible insofar as the capacity to bind to the Muc17 antigen remains. The antibody fragment used in the present invention preferably comprises either the heavy chain variable region (VH) or the light chain variable region (VL) or both. The amino acid sequence of the VH or VL region may comprise a substitution, deletion, addition, and/or insertion. Moreover, a portion of the VH or VL region or both can also be deleted, insofar as the capacity to bind to the Muc17 antigen remains. The variable region may also be a chimeric or humanized one. Specific examples of antibody fragments are Fab, Fab', F(ab')2, and Fv. Specific examples of low molecular weight antibodies are Fab, Fab', F(ab')2, Fv, scFv (single chain Fv), diabody, and sc(Fv)2 (single chain (Fv)2). Multimers of these antibodies (e.g., dimers, trimers, tetramers, polymers) are also encompassed by the low molecular weight antibodies of the present invention.

The antibody fragments can be obtained by the enzymatic treatment of an antibody. For example, papain, pepsin and plasmin are the enzymes known to be used for producing an antibody fragment. Or, a gene encoding such an antibody fragment can be constructed and inserted into an expression vector, and expressed in a suitable host cell (see, for example, to Co, M. S. et al., J. Immunol. (1994) 152, 2968-2976; Better, M. & Horwitz, A. H. Methods in Enzymology (1989) 178, 476-496; Plueckthun, A. & Skerra, A. Methods in Enzymology (1989) 178, 476-496; Lamoyi, E. Methods in Enzymology (1989) 121, 652-663; Rousseaux, J. et al., Methods in Enzymology (1989) 121, 663-669; and Bird, R. E. et al., TIBTECH (1991) 9, 132-137).

Diabody refers to a bivalent antibody fragment that is constructed by gene fusion (Holliger, P. et al., Proc. Natl. Acad. Sci. USA 90, 6444-6448 (1993), EP 404,097, WO 93/11161, and so forth). A diabody is a dimer built up from two polypeptide chains. In general, each of the polypeptide chains constituting a diabody comprises VL and VH regions ligated by a linker. The linker for a diabody is generally sufficiently short such that the VL and VH regions are unable to bind to each other. In specific terms, for example, the linker consists of about five amino acid residues, so that the VL and VH regions on the same polypeptide chain are unable to form a single chain variable region fragment but will form a dimer with a separate single chain variable region fragment. As a result, a diabody has two antigen binding sites.

scFv is obtained by ligating an H chain V region of an antibody to an L chain V region. The H chain V region and L chain V region in scFv are ligated to each other through a linker, preferably through a peptide linker (Huston, J. S. et al., Proc. Natl. Acad. Sci. USA, 85, 5879-5883 (1988)). The H chain V region and L chain V region in the scFv may originate from any antibodies described herein. There are no particular limitations on the peptide linker that links the V regions. For example, any single peptide chain having from about 3 to 25 residues can be used as a linker.

sc(Fv)2 is a low molecular weight antibody in which two VHs and two VLs are linked by a linker into a single chain (Hudson et al., J. Immunol. Methods, 231:177-189 (1999)). sc(Fv)2 can be constructed, for example, by linking scFvs with a linker.

The antibody of the present invention can also be used in the form of a modified antibody where various molecules such as polyethylene glycol (PEG) or a cytotoxin is attached to the antibody. Such a modified antibody can be obtained by a chemical modification of an antibody of the present invention. Methods for modifying antibodies have already been established in the art.

A cytotoxin to be attached to the antibody of the present invention may include, for example, toxins, radioactive substances, chemotherapeutic agents, and so forth. The cytotoxin encompasses prodrugs, which are converted in vivo into an active cytotoxin. Prodrug activation may proceed through an enzymatic or non-enzymatic conversion. As used herein, a toxin denotes various proteins and polypeptides derived from microbial, plant, or animal origin, that exhibit cytotoxicity. As used herein, a radioactive substance refers to a substance that contains a radioisotope. There are no particular limitations on the radioisotope and any radioisotope may be used in the present invention. As used herein, a chemotherapeutic agent denotes a substance, other than the toxin and radioactive substance as described above, that exhibits a cytotoxic activity. The chemotherapeutic agents may include, for example, cytokines, anti-tumor agents, enzymes, and so forth.

The antibody of the present invention may also be a bispecific antibody. A bispecific antibody is an antibody that has, within the same antibody molecule, variable regions that recognize different epitopes. Such epitopes may be present in different molecules or may be present in a single molecule. Thus, in the context of the present invention, a bispecific antibody may have antigen binding sites that recognize different epitopes on the Muc17 protein. With such a bispecific antibody, two antibody molecules can bind to one Muc17 molecule, whereby a stronger cytotoxicity is expected. Such antibodies are also encompassed by the "antibody" according to the present invention.

The present invention also encompasses a bispecific antibody that recognizes an antigen other than Muc17. For example, the present invention encompasses a bispecific antibody that recognizes an antigen different from Muc17, wherein the antigen is specifically expressed on the cell surface of target cancer cells as with Muc17.

Methods of producing bispecific antibodies are known in the art. For example, a bispecific antibody can be produced by joining two antibodies that recognize different antigens. Each of the joined antibodies may be a half-molecule that has an H chain and an L chain or may be a quarter-molecule that has only an H chain. Alternatively, a fused cell that produces bispecific antibody can also be prepared by fusing hybridomas that produce different monoclonal antibodies. Bispecific antibodies may also be produced by genetic engineering techniques.

Antibody Production Methods

The anti-Muc17 antibody according to the present invention can be obtained using known means. Monoclonal antibody of mammalian origin is particularly preferred for the anti-Muc17 antibody of the present invention. Monoclonal antibodies of mammalian origin encompass, inter alia, a monoclonal antibody produced by a hybridoma and a monoclonal antibody produced by a host transformed by genetic engineering techniques with an expression vector that contains the antibody gene.

Monoclonal antibody-producing hybridomas can be prepared using known technology, for example, as described below. An animal is first immunized with a Muc17 protein as the sensitizing antigen according to conventional immunization methods. Immune cells obtained from the immunized animal are fused with a known partner cell by conventional cell fusion techniques to obtain hybridomas. Hybridomas producing anti-Muc17 antibody can be screened using conventional screening techniques.

In specific terms, a monoclonal antibody can be produced as follows. First, the Muc17 protein to be used as the sensitizing antigen for antibody generation can be obtained by the expression of Muc17 gene. The nucleotide sequence of the human Muc17 gene is disclosed, for example, as GenBank accession number NM_001040105 (SEQ ID NO:1). The nucleotide sequence encoding Muc17 is inserted into a known expression vector and a suitable host cell is then transformed with the expression vector. The desired human Muc17 protein can be purified from the host cells or from the culture supernatant. Purified naturally occurring Muc17 protein can also be used in the same manner. The Muc17 protein is purified using a single or a combination of conventional chromatographic techniques, e.g., ion chromatography, affinity chromatography, and so forth, with a single run or a plurality of runs. The immunogen used in the present invention can also be a fusion protein, which may be obtained by fusion of a desired partial polypeptide from the Muc17 protein with a different polypeptide. For example, a peptide tag or the Fc fragment from the antibody can be used to produce the fusion protein to be used as the immunogen. A vector that expresses the fusion protein can be prepared by in-frame fusion of the genes encoding the desired two or more polypeptide fragments, and the fused gene is inserted into an expression vector as described above. Methods for producing fusion proteins are described in, for example, Sambrook, J. et al., "Molecular Cloning" 2nd Edition, 9.47-9.58, Cold Spring Harbor Laboratory Press, 1989.

The Muc17 protein purified as above can be employed as the sensitizing antigen to immunize a mammal. A partial peptide from Muc17 can also be used as the sensitizing antigen. For example, the following peptides can be used as the sensitizing antigen:

a peptide obtained by chemical synthesis based on the amino acid sequence of human Muc17;

a peptide obtained by incorporating a portion of the human Muc17 gene into an expression vector and expressing same; and a peptide obtained by degradation of human Muc17 protein with a protein degrading enzyme.

There are no limitations on the region or the size of the partial peptide of Muc17. A preferred region can be selected from the amino acid sequence constituting the extracellular domain of Muc17 (positions 1 to 4389 in the amino acid sequence of SEQ ID NO:2). The number of amino acids making up the peptide to be used as the sensitizing antigen comprises preferably at least 3, at least 5 or at least 6 residues. More specifically, a peptide of 8 to 50 residues, preferably 10 to 30 residues may be used as the sensitizing antigen.

There are no particular limitations on the mammal species to be immunized by the sensitizing antigen described above. In order to obtain monoclonal antibody by cell fusion techniques, the immunized animal is preferably selected considering the compatibility with the partner cell used in the cell fusion process. Rodents are generally preferred as the immunized animal. Specifically, mouse, rat, hamster, or rabbit can be used as the immunized animal. Monkeys can also be used as the immunized animal.

The animal as described above can be immunized with the sensitizing antigen according to known methods. In general, for example, the mammal is immunized by subcutaneous or intraperitoneal injection of the sensitizing antigen. In specific terms, the sensitizing antigen may be administered to the mammal several times on 4-21 day intervals. The sensitizing antigen is diluted by a suitable dilution factor with, for example, phosphate-buffered saline (PBS) or physiological saline. The sensitizing antigen may also be administered in combination with an adjuvant. For example, the sensitizing antigen can be prepared by mixing and emulsification with Freund's complete adjuvant. A suitable carrier may also be used upon immunization with the sensitizing antigen. Particularly in those instances where a low molecular weight partial peptide is used as the sensitizing antigen in immunization, the sensitizing peptide antigen is preferably conjugated with a protein carrier, such as albumin, keyhole limpet hemocyanin, and so forth.

After the mammal is immunized as above, and the serum antibody titer is desirably elevated, immune cells are collected from the animal and subjected to cell fusion. In particular, splenocytes are preferred immune cells.

Mammalian myeloma cells are used as the cells for fusion with the above-described immune cells. The myeloma cells are preferably provided with a suitable selection marker to facilitate screening. The selection marker denotes a trait that can appear (or that cannot appear) under specific culture conditions. Known selection markers include hypoxanthine-guanine phosphoribosyl transferase deficiency (abbreviated below as HGPRT deficiency) and thymidine kinase deficiency (abbreviated below as TK deficiency). HGPRT- or TK-deficient cells will exhibit hypoxanthine-aminopterin-thymidine sensitivity (abbreviated below as HAT sensitivity). HAT-sensitive cells are unable to undergo DNA synthesis on HAT selection medium and will die. When fused with a normal cell, DNA synthesis will continue utilizing the salvage pathway of the normal cell and the fused cells will grow on HAT selection medium.

HGPRT-deficient cells can be selected on a medium containing 6-thioguanine or 8-azaguanine (8AG), while TK-deficient cells can be selected on a medium containing 5'-bromodeoxyuridine. Normal cells incorporate these pyrimidine analogues into their DNA and will die, while cells deficient in these enzymes do not incorporate the pyrimidine analogs and are able to survive on the selection medium. Another selection marker, known as G418 resistance, imparts resistance to 2-deoxystreptamine-type antibiotics (gentamycin analogues) due to the presence of the neomycin resistance gene. Various myeloma cells suitable for cell fusion are known. For example, the following myeloma cells may be employed: P3 (P3x63Ag8.653) (J. Immunol. (1979) 123, 1548-1550), P3x63Ag8U.1 (Current Topics in Microbiology and Immunology (1978) 81, 1-7), NS-1 (Kohler, G. and Milstein, C. Eur. J. Immunol. (1976) 6, 511-519), MPC-11 (Margulies, D. H. et al., Cell (1976) 8, 405-415), SP2/0 (Shulman, M. et al., Nature (1978) 276, 269-270), FO (de St. Groth, S. F. et al., J. Immunol. Methods (1980) 35, 1-21), S194 (Trowbridge, I. S. J. Exp. Med. (1978) 148, 313-323), and R210 (Galfre, G. et al., Nature (1979) 277, 131-133).

Cell fusion between the above-described immune cells and myeloma cells can be carried out according to known methods, for example, the method of Kohler and Milstein (Kohler, G. and Milstein, C., Methods Enzymol. (1981) 73, 3-46).

More specifically, the cell fusion can be carried out, for example, in conventional nutrient culture medium in the presence of a cell fusion promoter. For example, polyethylene glycol (PEG) or Sendai virus (HVJ) can be used as the fusion promoter. As desired, an auxiliary such as dimethyl sulfoxide can be added in order to enhance the fusion efficiency.

The ratio of the immune cells to the myeloma cells may be suitably selected. For example, the immune cells are preferably used at from 1 to 10-fold with respect to the myeloma cells. The culture medium used for cell fusion is, for example, RPMI1640 culture medium or MEM culture medium, which are suitable for the growth of the myeloma cell lines mentioned above, or may be conventional culture media used for this type of cell culture. A serum supplement such as fetal calf serum (FCS) can also be added to the culture medium.

To obtain fused cells (hybridomas) by cell fusion, prescribed quantities of the immune cells and myeloma cells are thoroughly mixed in a culture medium as described above and a PEG solution preheated to about 37° C. is added. For example, PEG with an average molecular weight of 1000 to 6000 can be added at a concentration typically from 30 to 60% (w/v). Then, the cell fusion agents and other components that are undesirable for growth of hybridoma are removed by adding a suitable culture medium as described above, centrifuging, and removing the supernatant, and repeating the process as necessary.

The hybridomas obtained as above can be screened using a selection medium adapted to the selection markers intrinsic to the myeloma used for cell fusion. For example, HGPRT- or TK-deficient cells can be selected by culture on HAT medium (medium containing hypoxanthine, aminopterin, and thymidine). Thus, when HAT-sensitive myeloma cells are used for cell fusion, cells fused to the normal cells can selectively grow on the HAT medium. Culture on the HAT medium is continued for a period of time sufficient for cells (unfused cells) other than the desired hybridomas to die. In specific terms, the desired hybridomas can be selected generally by culture for from several days to several weeks. Conventional limit dilution process may be applied for screening and monocloning of hybridomas that produce the desired antibody. Alternatively, an antibody that recognizes Muc17 can also be obtained by the method described in WO 03/104453.

Screening and monocloning of the desired antibody can be suitably carried out by a screening procedure based on known antigen-antibody reactions. For example, an antigen may be bound to a carrier (e.g., polystyrene beads or a commercial 96-well microtiter plate) and then reacted with hybridoma culture supernatant. After the carrier is washed, an enzyme-labeled secondary antibody is added. If the desired sensitizing antigen-reactive antibody is present in the culture supernatant, the secondary antibody will bind to the carrier through the antibody. The presence/absence of the desired antibody in the culture supernatant can finally be determined by detection of the secondary antibody bound to the carrier. A hybridoma that produces the desired antigen-binding antibody can be cloned, for example, by the limit dilution method. In the detection, the protein used for immunization as well as a substantially the same Muc17 protein is suitably used as the antigen. For example, an oligopeptide comprising the extracellular domain of Muc17 or a partial amino acid sequence in the extracellular domain can be used as the antigen.

In addition to the above-described method of producing a hybridoma by immunizing a non-human animal with the antigen, the antibody of interest may also be obtained by sensitization of human lymphocytes with the antigen. In specific terms, human lymphocytes are first sensitized in vitro with the Muc17 protein. The immunosensitized lymphocytes are then fused with a suitable fusion partner. For example, myeloma cells of human origin having a permanent cell division capacity can be used as the fusion partner (see, JP C 01-59878). The anti-Muc17 antibody obtained by this method is a human antibody that has the capacity to bind to the Muc17 protein.

Human anti-Muc17 antibody can also be obtained by administering Muc17 protein as antigen to a transgenic animal that has the entire human antibody gene repertoire. Antibody-producing cells from the immunized animal can be immortalized by cell fusion with a suitable fusion partner or by infection with Epstein-Barr virus. Human antibody against the Muc17 protein can be isolated from the resulting immortalized cells (see WO 94/25585, WO 93/12227, WO 92/03918, and WO 94/02602). Moreover, cells that produce antibody having the desired reaction specificity can be isolated by cloning the immortalized cells. When a transgenic animal is employed as the immunized animal, the animal's immune system recognizes human Muc17 as a foreign substance. In this way, a human antibody directed to human Muc17 can be readily obtained. The monoclonal antibody-producing hybridoma constructed in the manner described above can be subcultured in conventional culture media. The hybridoma may be stored for a long time in liquid nitrogen.

Another technology is also known for obtaining human antibodies by a panning process using a human antibody library. For example, the human antibody V region can be expressed as a single chain antibody (scFv) on the surface of a phage by the phage display method, and phage that binds to an antigen can be selected. The genes of the selected phage is analyzed to determine the DNA sequence encoding the V region of human antibody that binds to the antigen. Once the DNA sequence of the antigen-binding scFv is determined, the V region sequence can be fused in-frame with a sequence encoding a human antibody C region. The fused gene is inserted into an appropriate expression vector, and transfected into an appropriate expression cell as described above, whereby a human antibody can be obtained by expression of the gene coding for the human antibody. Such methods are already known in the art (see WO 92/01047, WO 92/20791, WO 93/06213, WO 93/11236, WO 93/19172, WO 95/01438, and WO 95/15388).

The aforementioned hybridoma can be cultured according to conventional methods and the desired monoclonal antibody can be obtained from the resulting culture supernatant. Alternatively, the hybridoma is injected into a mammal compatible with the hybridoma to allow for growth, then a monoclonal antibody can be obtained from the ascites fluid of the animal. The former method is well suited for the production of high-purity antibody.

Recombinant Antibody

The antibody of the present invention can also be a recombinant antibody, which is prepared using an antibody gene cloned from the antibody-producing cell. Antibody expression can be achieved by incorporating the cloned antibody gene into a suitable vector followed by transfection into a host. Methods have already been established for isolating the antibody gene and inserting it into a vector and for transforming the host cell (see, for example, to Vandamme, A. M. et al., Eur. J. Biochem. (1990) 192, 767-775).

For example, cDNA encoding the variable region (V region) of the anti-Muc17 antibody can be isolated from a hybridoma cell that produces the anti-Muc17 antibody. Typically the total RNA is first extracted from the hybridoma. Methods for extracting mRNA from cells include, for example, the guanidine ultracentrifugal method (Chirgwin, J. M. et al., Biochemistry (1979) 18, 5294-5299) and the AGPC method (Chomczynski, P. et al., Anal. Biochem. (1987) 162, 156-159).

The extracted mRNA can be purified using, for example, an mRNA Purification Kit (GE Healthcare Biosciences). Kits for the direct extraction of the total mRNA from cells are also commercially available, such as the QuickPrep mRNA Purification Kit (GE Healthcare Biosciences). The total mRNA can be isolated from hybridomas using such kits. cDNA encoding the antibody V region can be synthesized from the obtained mRNA using reverse transcriptase. The cDNA can be synthesized with, for example, an AMV Reverse Transcriptase First-strand cDNA Synthesis Kit (Seikagaku Corporation). In addition, a 5'-AmpliFINDER RACE Kit (Clontech) and the PCR-based 5'-RACE method (Frohman, M. A. et al., Proc. Natl. Acad. Sci. USA (1988) 85, 8998-9002; Belyaysky, A., et al., Nucleic Acids Res. (1989) 17, 2919-2932) can be used for synthesizing and amplifying the cDNA. Moreover, suitable restriction sites can be introduced at both ends of the cDNA during the cDNA synthesis procedure, as described below.

The target cDNA fragment is purified from the obtained PCR product and is then ligated with the vector DNA. The recombinant vector constructed in this manner is transfected into, for example, E. coli. Colonies are selected and the desired recombinant vector can be prepared from the E. coli colony. In addition, known methods such as dideoxynucleotide chain termination method can be used to confirm that the recombinant vector contains the nucleotide sequence of the target cDNA.

PCR using variable region gene amplification primers can also be employed to obtain a gene that encodes the variable region. First, cDNA is synthesized from the extracted mRNA as a template to create a cDNA library. A commercially available kit is conveniently used to synthesize the cDNA library. Typically the amount of mRNA obtained from only a small number of cells is quite small, and its direct purification will provide a low yield. Thus mRNA is generally purified with the addition of carrier RNA that clearly does not contain the antibody gene. In those cases where a certain amount of RNA can be extracted, an efficient purification can be achieved even with RNA preparation only from the antibody-producing cells. For example, in some cases it may not be necessary to add carrier RNA for purifying the RNA preparation from at least 10 or at least 30 and preferably at least 50 antibody-producing cells.

The antibody gene can be amplified by PCR using the obtained cDNA library as a template. Primers for the PCR-based amplification of antibody genes are known in the art. For example, primers for the amplification of human antibody genes can be designed based on the information in the literature (for example, J. Mol. Biol. (1991) 222, 581-597). These primers have a nucleotide sequence that varies with the immunoglobulin subclass. Thus, when a cDNA library of unknown subclass is employed as a template, PCR is carried out considering all the possible subclasses.

In specific terms, in order to isolate genes encoding human IgG, primers can be selected to have the ability to amplify genes encoding γ1 to γ5 for the heavy chain and the κ chain and λ chain for the light chain. In order to amplify the IgG variable region gene, a primer that anneals to the region corresponding to the hinge region is ordinarily used for the 3'-side primer. On the other hand, a primer adapted for each subclass can be used for the 5'-side primer.

The PCR products based on gene amplification primers for each heavy chain and light chain subclass are made as separate libraries. Using the libraries thus synthesized, immunoglobulin comprising a combination of heavy chain and light chain can be reconstructed. The desired antibody can be screened for the binding activity of the reconstructed immunoglobulin for Muc17.

Binding to Muc17 by the antibody of the present invention is preferably a specific binding. An antibody that binds Muc17 can be screened, for example, by the following steps:
(1) bringing Muc17 into contact with an antibody containing a V region encoded by cDNA obtained from the hybridoma;
(2) detecting binding between Muc17 and the antibody; and
(3) selecting an antibody that binds to Muc17.

Methods of detecting binding between an antibody and Muc17 are known. In specific terms, the test antibody is reacted with Muc17 immobilized on a carrier and then reacted with a labeled antibody that recognizes the test antibody. After washing, if the labeled antibody is detected on the carrier, it indicates that the test antibody binds to Muc17. The antibody may be labeled with a fluorescent substance such as FITC or an enzymatic protein such as peroxidase or β-galactoside. Also fixed form of Muc17-expressing cells can be used to evaluate the antibody's binding activity.

Panning process using a phage vector can also be employed as a method of antibody screening based on the binding activity. Screening with a phage vector is advantageous when the antibody gene libraries are prepared for separate libraries for the heavy chain subclass and the light chain subclass as described above. The genes encoding the heavy chain and light chain variable regions are linked via a suitable linker sequence to form a single-chain Fv (scFv). The scFv-encoding genes may be inserted into a phage vector to obtain phage that expresses scFv on its surface. The phage is brought into contact with the target antigen, and the phage bound to the antigen is collected to obtain DNA coding for scFv with the desired binding activity. scFv having the desired binding activity can be enriched by repeating this process as necessary.

Once the cDNA encoding the V region of the target anti-Muc17 antibody is obtained, cDNA is digested by restriction enzymes that recognize the restriction sites present at both ends of the cDNA. Preferred restriction enzymes will recognize and digest at nucleotide sequences that occurs with lower frequency within the nucleotide sequence of the antibody gene. In addition, in order to insert one copy of the digestion fragment in the correct direction into the vector, the restriction enzyme preferably provides cohesive ends. An antibody expression vector can be obtained by inserting the cDNA encoding the anti-Muc17 antibody V region, digested as described above, into a suitable expression vector. A gene encoding the antibody constant region (C region) is fused in-flame with the aforementioned V region-encoding gene to obtain a chimeric antibody. As used herein, a chimeric antibody refers to a product having different origins for the constant region and variable region. Thus in the context of the present invention, "a chimeric antibody" encompasses a heterochimeric antibody such as a mouse-human chimera, as well as a human-human allochimeric antibody. A chimeric antibody expression vector can also be constructed by inserting the aforementioned V region gene into an expression vector that already carries the constant region gene.

More specifically, for example, an expression vector that carries DNA encoding the desired antibody constant region (C-region) may be constructed to contain at the 5' side of the C-region a restriction enzyme recognition sequence for the restriction enzyme used for digesting the V-region gene. The two fragments are digested with the same restriction enzyme and fused in-frame to construct a chimeric antibody expression vector.

In order to produce the anti-Muc17 antibody of the present invention, the antibody gene can be incorporated in the expression vector in such a manner that expression occurs under the control of an expression control region. Expression control regions for antibody expression include, for example, enhancers and promoters. Recombinant cells that express DNA coding for anti-Muc17 antibody can then be obtained by transforming suitable host cells with the expression vector.

For expression of the antibody gene, the DNA coding for the antibody heavy chain (H chain) and the DNA coding for the antibody light chain (L chain) can be incorporated in separate expression vectors. An antibody molecule provided with H and L chains can be expressed by simultaneously transforming (co-transfect) the same host cell with the vector incorporating the H chain and the vector incorporating the L chain. Alternatively, DNA encoding the H chain and L chain may be incorporated in a single expression vector and the host cell may be transformed (WO 94/11523).

Numerous host/expression vector combinations are known for use in antibody production by isolating the antibody gene and transfecting a suitable host. Any of these expression systems may be applied to the present invention. Animal cells, plant cells, or fungal cells can be used when eukaryotic cells are used as the host. Specific examples of animal cells that can be used in the present invention include mammalian cells (e.g., CHO, COS, myeloma, baby hamster kidney (BHK), Hela, Vero, and so forth), amphibian cells (e.g., *Xenopus laevis* oocytes and so forth), and insect cells (e.g., sf9, sf21, Tn5, and so forth).

In the case of plant cells, antibody gene expression systems based on cells from genus *Nicotiana*, e.g., *Nicotiana tabacum*, are known. Callus-cultured cells can be used for plant cell transformation.

As a fungal cell, the following cells can be used: yeast (e.g., *Saccharomyces* such as *Saccharomyces cerevisiae*, *Pichia* such as *Pichia pastoris*, and so forth), and filamentous fungi (e.g., *Aspergillus* such as *Aspergillus niger*).

Antibody gene expression systems using prokaryotes are also known. For example, bacteria such as *E. coli, Bacillus subtilis*, and so forth, can be used in the present invention.

When a mammalian cell is used, an expression vector can be constructed by operably linking a commonly used effective promoter, the antibody gene to be expressed, and a polyA signal downstream at the 3' side of the antibody gene. An example of a promoter/enhancer is human cytomegalovirus immediate early promoter/enhancer.

Other promoter/enhancers that can be used to express the antibody of the present invention include, for example, viral promoter/enhancers and promoter/enhancers that originate in mammalian cells, such as human elongation factor 1α (HEF1α). Specific examples of viruses that can provide usable promoter/enhancers are retroviruses, polyoma viruses, adenoviruses, and simian virus 40 (SV40).

The SV40 promoter/enhancer can be used according to the method of Mulligan et al. (Nature (1979) 277, 108). In addition, the HEF1α promoter/enhancer can be readily utilized for gene expression according to the method of Mizushima et al. (Nucleic Acids Res. (1990) 18, 5322).

In the case of *E. coli*, expression of the gene can be achieved by operably linking an effective, commonly used promoter, a signal sequence for antibody secretion, and the antibody gene to be expressed. The promoter can be, for example, lacZ promoter or araB promoter. The lacZ promoter can be used according to the method of Ward et al. (Nature (1989) 341, 544-546; FASEBJ. (1992) 6, 2422-2427). The araB promoter can be used for gene expression according to the method of Better et al. (Science (1988) 240, 1041-1043).

With regard to the signal sequence for antibody secretion, the pelB signal sequence (Lei, S. P. et al., J. Bacteriol. (1987) 169, 4379) may be used in the case of production into the *E. coli* periplasm. After the antibody produced in the periplasm is isolated, the antibody structure can be reorganized (refolded) by the use of a protein denaturant such as urea guanidine hydrochloride so as to exhibit the desired binding activity.

The origin of replication on the expression vector can be, for example, an origin of replication originating in SV40, polyoma virus, adenovirus, bovine papilloma virus (BPV), and so forth. In addition, a selection marker can be inserted in the expression vector for amplification of the gene copy number in the host cell system. In specific terms, usable selection markers include the aminoglycoside transferase (APH) gene, the thymidine kinase (TK) gene, the *E. coli* xanthine-guanine phosphoribosyl transferase (Ecogpt) gene, the dihydrofolate reductase (dhfr) gene, and so forth.

The target antibody can be produced by transfecting the expression vector into a host cell and culturing the transformed host cell in vitro or in vivo. Host cell culture can be carried out according to known methods. For example, DMEM, MEM, RPMI1640, or IMDM can be used as the culture medium; a serum supplement such as fetal calf serum (FCS) can also be added.

The antibody expressed and produced as described above can be purified by conventional methods known for protein purification. Such method can be used alone or in combination. The antibody can be isolated and purified using suitable selections and combinations of, for example, an affinity column (for example, a protein A column), column chromatography, filtration, ultrafiltration, salting out, dialysis, and so forth (Antibodies: A Laboratory Manual. by Ed Harlow and David Lane, Cold Spring Harbor Laboratory, 1988).

In addition to host cells as described above, transgenic animals can also be used to produce recombinant antibodies. A gene encoding the target antibody is introduced into a transgenic animal and the target antibody can be obtained from the animal. For example, a fused gene can be constructed by inserting in-flame the antibody gene into a gene coding for a protein that is naturally produced in milk. For example, goat β-casein can be used as the protein secreted into milk. A DNA fragment containing the fused gene bearing the antibody gene may be injected into a goat embryo and the injected embryo may be introduced into a female goat. The desired antibody can be isolated as a fusion protein with the milk protein from the milk produced by the transgenic goat born from the embryo-implanted goat (or its offspring). In addition, hormones can be administered as appropriate to the transgenic goat in order to increase the amount of milk containing the desired antibody produced by the transgenic goat (Ebert, K. M. et al., Bio/Technology (1994) 12, 699-702).

C regions originating in animal antibodies can be used as the C region of the recombinant antibody of the present invention. The mouse antibody H chain C regions designated Cγ1, Cγ2a, Cγ2b, Cγ3, Cμ, Cδ, Cα1, Cα2, and Cε, and the L chain C regions designated as Cκ and Cλ can be used. Animal antibodies from, for example, rat, rabbit, goat, sheep, camel, monkey, and so forth, can be used as animal antibodies other than mouse antibodies. These sequences are known. The C region can be modified in order to improve the stability of antibody or its production.

Pharmaceutical Composition

The present invention provides a pharmaceutical composition comprising the anti-Muc17 antibody as an effective ingredient. The present invention also relates to an anti-cancer agent comprising the anti-Muc17 antibody as an effective ingredient. The anti-cancer agent of the present invention is preferably administered to a subject suffering from cancer or to a subject at risk for recurrence of cancer.

In addition to the anti-cancer agent comprising the anti-Muc17 antibody as an effective ingredient, the present invention also provides a method of preventing or treating cancer comprising a step of administering the anti-Muc17 antibody to a subject, as well as the use of the anti-Muc17 antibody for the production of an anti-cancer agent.

There are no particular limitations on the type of cancer to be treated by the anti-cancer agent of the present invention, but in general the cancer is that expressing Muc17 protein, preferably pancreatic cancer or colon cancer.

As used herein, the phrase "comprising an anti-Muc17 antibody as an effective ingredient" means that the anti-Muc17 antibody is contained as a primary active ingredient, but not limit the contents of the monoclonal antibody.

The pharmaceutical composition of the present invention and the anti-cancer agent of the present invention may comprise a plurality of antibody species as necessary. For example, it may be possible to enhance the cytotoxic activity against Muc17-expressing cells by using a cocktail of a plurality of anti-Muc17 antibodies. In addition, it may also be possible to increase the treatment efficacy by combining the anti-Muc17 antibody with an antibody that recognizes another tumor-associated antigen. The pharmaceutical composition of the present invention may comprise the anti-Muc17 antibody and another antibody that recognizes the anti-Muc17 antibody, for example, an anti-human IgG antibody. Preferably, a cytotoxic substance, e.g., a toxin, radioactive substance, chemotherapeutic agent, and so forth, is attached to the antibody recognizing the anti-Muc17 antibody, such as an anti-human IgG antibody.

The pharmaceutical composition of the present invention or the anti-cancer agent of the present invention may be administered to the patient either orally or parenterally, and parenteral administration is preferred. Specific routes of administration may include injection, transnasal administration, transpulmonary administration, transdermal administration, and so forth. With regard to administration by injection, the pharmaceutical composition of the present invention can be administered systemically or locally by, for example, intravenous injection, intramuscular injection, intraperitoneal injection, or subcutaneous injection. The appropriate mode of administration can be selected depending on the age and symptoms of the patient. The dosage may be selected, for example, from the range of 0.0001 mg to 1000 mg per 1 kg body weight per administration. Alternatively, the dosage may be selected from the range of 0.001 to 100000 mg/body per patient. However, the pharmaceutical composition of the present invention is not limited to the preceding dosages.

The pharmaceutical composition of the present invention can be formulated according to conventional methods (see, for example, Remington's Pharmaceutical Science, latest edition, Mack Publishing Company, Easton, USA). It may comprise a pharmaceutically acceptable vehicle and pharmaceutically acceptable additives, including, for example, surfactants, excipients, colorants, flavors, preservatives, stabilizers, buffers, suspending agents, tonicity agents, binders, disintegrants, lubricants, fluidity promoters, taste-masking agents, and so forth. However, there is no limitation and other generally used vehicles can be employed as appropriate. Specific examples of vehicles are light silicic anhydride, lactic acid, crystalline cellulose, mannitol, starch, carmellose calcium, carmellose sodium, hydroxypropyl cellulose, hydroxypropylmethyl cellulose, polyvinyl acetal diethylamino acetate, polyvinylpyrrolidone, gelatin, medium-chain fatty acid triglycerides, polyoxyethylene hardened castor oil 60, sucrose, carboxymethyl cellulose, corn starch, inorganic salts, and so forth.

The present invention also provides a method of damaging Muc17-expressing cells or a method of inhibiting cell growth, by contacting Muc17-expressing cells with the anti-Muc17 antibody. The anti-Muc17 antibody is as described above. There is no particular limitation on the cells to be bound by the anti-Muc17 antibody as long as the cells are expressing Muc17. In the present invention, Muc17-expressing cell is preferably a cancer cell. Examples of preferred cancer cell are pancreatic cancer cell and colon cancer cell.

As used herein, "contact" may be carried out in vitro or in vivo. For example, contact may be effected by adding the antibody to the culture medium of Muc17-expressing cells in a test tube. The antibody may be added in the form of solution or in the form of a solid obtained by freeze-drying. In those instances where the antibody is added in the form of an aqueous solution, such an aqueous solution may comprise only the pure antibody or may also comprise, for example, surfactant, excipient, colorant, flavor, preservative, stabilizer, buffer, suspending agent, tonicity agent, binder, disintegrant, lubricant, fluidity promoter, taste-masking agent, and so forth, as described above. While there are no particular limitations on the amount to be added, suitable final concentrations in the culture medium are preferably 1 pg/mL to 1 g/mL, more preferably 1 ng/mL to 1 mg/mL, and even more preferably 1 µg/mL to 1 mg/mL.

In another embodiment of the present invention, "contact" may also be carried out by administration to a non-human animal bearing Muc17-expressing cells which have been implanted, transplanted, or grafted, or by administration to an animal that inherently has Muc17-expressing cancer cells. The mode of administration may be oral administration or parenteral administration. Parenteral administration is particularly preferred. Specific routes of administration include injection, transnasal administration, transpulmonary administration, transdermal administration, and so forth. With regard to administration by injection, the cell proliferation inhibitor or anti-cancer agent of the invention can be administered systemically or locally by, for example, intravenous injection, intramuscular injection, intraperitoneal injection, or subcutaneous injection. The appropriate mode of administration can be selected depending on the age and symptoms of the animal subject. In those instances where an aqueous solution is administered, such an aqueous solution may comprise only the pure antibody or may also comprise, for example, surfactant, excipient, colorant, flavor, preservative, stabilizer, buffer, suspending agent, tonicity agent, binder, disintegrant, lubricant, fluidity promoter, taste-masking agent, and so forth, as described above. The dosage may be selected, for example, from the range of 0.0001 mg to 1000 mg per 1 kg body weight per administration. Alternatively, the dosage may be selected from the range, for example, of 0.001 to 100000 mg/body per patient. However, the dosage of the antibody of the present invention is not limited to the preceding dosages.

Diagnostic Method

The present invention further provides a method of diagnosing cancer using anti-Muc17 antibody. There are no particular limitations on the cancer to be diagnosed by the method of the present invention as long as it expresses Muc17. Pancreatic cancer and colon cancer are preferred.

The diagnostic method of the present invention may be carried out in vitro or in vivo, with in vitro being preferred.

The method of the present invention of diagnosing cancer using anti-Muc17 antibody comprises, for example, the steps of:

(a) providing a sample collected from a subject; and
(b) detecting Muc17 protein present in the sample from (a).

As used herein detection encompasses quantitative detection and qualitative detection. Examples of qualitative detection include, for example, measurement as to whether Muc17 protein is present, measurement as to whether Muc17 protein is present in an amount greater than or equal to a given amount, and comparison of the amount of Muc17 protein with another sample (for example, a control sample). Quantitative detection include, for example, measurement of the Muc17 protein concentration and measurement of the amount of Muc17 protein.

There are no particular limitations on the test sample insofar as the sample is suspected to contain the Muc17 protein. A sample collected from the body of a living organism such as a mammal is particularly preferred. More preferably, a sample is collected from a human. Specific examples of the test sample include blood, interstitial fluid, plasma, extravascular fluid, cerebrospinal fluid, synovial fluid, pleural fluid, serum, lymph fluid, saliva, urine, and tissue. Preferably the sample is obtained from a test sample such as a cell culture medium or a specimen provided by fixing tissue or cells collected from a living organism.

The Muc17 protein can be detected by methods known in the art, including, for example, radioimmunoassay (RIA), enzyme immunoassay (EIA), fluorescent immunoassay (FIA), luminescent immunoassay (LIA), immunoprecipitation (IP) methods, turbidimetric immunoassay (TIA) methods, western blotting (WB), immunohistochemical (IHC) methods, and immunodiffusion methods (SRID).

The contents of all the patents and references explicitly cited in the application are hereby incorporated by reference in its entirety.

EXAMPLES

The present invention is described in greater detail by the examples provided below, but the present invention is not limited by these examples.

Example 1

Expression Analysis of Mucin 17 (Muc17) mRNA Using Real-Time PCR

Cells from the pancreatic cancer cell lines AsPc1, Panc1, Capan1, and BxPC3 were purchased from the ATCC. They were cultured using the conditions described in the accompanying materials and the total RNA was prepared from $1 \times 10^7$ cells using Trizol (Invitrogen Corporation). 1 µg total RNA was treated with DNase I (Invitrogen Corporation) followed by cDNA synthesis using a SuperScript III First Strand Synthesis System for RT-PCR (Invitrogen Corporation) and using oligo(dT) primers. cDNA was also synthesized by the same method using the total RNA from each of the normal tissues shown in Table 1. Real-time PCR was carried out by the intercalation method using SYBR Green I. Briefly, using cDNA corresponding to 3.3 ng total RNA as template, 33 cycles of 5 seconds/95° C. and 30 seconds/60° C. were carried out on a 20 µL reaction solution containing SYBR (trademark) Premix Ex Taq (Takara Bio Inc.), sense primer (SEQ ID NO:30), and antisense primer (SEQ ID NO:31). A standard curve was constructed based on samples templated on previously purified PCR products and the amount of cDNA in the sample was calculated from the measured values. As shown in FIG. 1, Muc17 mRNA is highly expressed in AsPc1, a pancreatic cancer line. The expression in normal tissues was limited to the small intestine.

TABLE 1

Tissues used for Muc17 gene expression analysis

| Name | Company | CAT# |
|---|---|---|
| Brain, Cerebrum | Ambion | 6000 |
| Ovary | Ambion | 6000 |
| Pancreas | Ambion | 7954 |
| Thyroid | Ambion | 6000 |
| Testis | Ambion | 7972 |
| Breast | Stratagene | 540045 |
| Spleen | Ambion | 6000 |
| Tonsil | Clontech | 636587 |
| Thymus | Ambion | 6000 |
| Bone Marrow | Clontech | 636548 |
| Lung | Ambion | 7968 |
| Heart | Stratagene | 540011 |
| Esophagus | Ambion | 6000 |
| Stomach | Stratagene | 540037 |
| Small Intestine | Ambion | 6000 |
| Colon | Clontech | 636553 |
| Liver | Ambion | 6000 |
| Salivary Gland | Clontech | 636552 |
| Kidney | Ambion | 7976 |
| Prostate | Ambion | 6000 |
| Uterus | Stratagene | 540043 |
| Cervix | Ambion | 6000 |
| Skeletal Muscle | Ambion | 6000 |
| Skin | Stratagene | 540031 |
| Dorsal Root | Clontech | 636150 |
| Pericardium | Ambion | 6852 |
| Placenta | Ambion | 6000 |
| Peripheral Blood | Clontech | 636580 |
| Lymph Node | Stratagene | 540021 |
| Caval Vein | Stratagene | 540121 |
| Medulla Oblongata | Clontech | 636562 |
| Adipose | Ambion | 6000 |
| Bladder | Ambion | 6000 |
| Trachea | Ambion | 6000 |

Example 2

Construction of Anti-Muc17 Antibody 2.1 Cloning of cDNA Coding for a Human Muc17 Partial Sequence Muc17 (Accession No. NM_001040105) is a type 1 membrane protein comprising 4,493 amino acids (SEQ ID NOs:1 and 2). Muc17 belongs to the membrane-form mucin family, and most part of the extracellular domain comprises a repeat of serine-, threonine-, and proline-rich 59-mer tandem repeat sequence, and is glycosylated. In addition, it comprises an SEA domain (4182Glu-4287Asn), suggesting that the protein is cleaved and that at least a part of the protein may be present in the secreted form. The existence of a secreted-form splicing variant (same sequence in 1Met-4241Arg) has also been reported (Moniaux et al., J. Biol. Chem., 281 (2006) 23676-23685). The inventors prepared an anti-Muc17 antibody because an antibody specific to Muc17 but not capable of binding to the secreted-form of Muc17 could be a novel therapeutic agent for pancreatic cancer.

In order to construct an antibody highly specific to Muc17, a C-terminal partial sequence (Muc17ct, 4115Thr-4390Leu) within the extracellular domain of Muc17 (1Met-4389Ser) was cloned. Using the cDNA from AsPc1 as a template, a reaction solution containing a sense primer (SEQ ID NO:32) appended at the 5' end with an EcoRI recognition sequence and a mouse antibody signal sequence, an antisense primer (SEQ ID NO:33) appended with a CpoI recognition sequence, 10×KOD-Plus buffer, 2 mM dNTPs, 25 mM MgSO$_4$, and KOD-Plus (Takara Bio Inc.) was reacted in 5 cycles of 10 seconds/98° C., 5 seconds/72° C., and 4 minutes/68° C., 5 cycles of 10 seconds/98° C., 5 seconds/70° C., and 4 minutes/68° C., and 25 cycles of 10 seconds/98° C. and 4 minutes/68° C. The amplification product yielded by the PCR reaction was inserted into pGEM-T Easy using a pGEM-T Easy Vector System I (Promega Corporation). The sequence was analyzed using an ABI3730 DNA Analyzer.

2.2 Construction of Soluble Type of Human Muc17ct/Mouse IgG2a Fc Fusion Protein

The Muc17ct gene cloned into the pGEM-T Easy vector was digested with EcoRI and CpoI and was cloned into pMCDN_mIgG2aFc. pMCDN_mIgG2aFc is derived from the mammalian cell expression vector pMCDN. It contains the neomycin resistance gene and DHFR gene and its expression is inducible under the mouse CMV promoter (Accession No. U68299). In the vector pMCDN_mIgG2aFc, the Fc sequence of mouse H chain IgG2a containing the hinge and downstream region are inserted in the EcoRI and NotI recognition sites of the pMCDN vector, and Muc17ct and mIgG2aFc sequences are connected by the CpoI recognition sequence. The sequence shown in SEQ ID NO:34 gives the nucleotide sequence of Muc17ct_mIgG2aFc and the sequence shown in SEQ ID NO:35 gives the amino acid sequence of Muc17ct_mIgG2aFc.

pMCDN/Muc17ct_mIgG2aFc was transfected by electroporation into DG44 cells (Invitrogen Corporation) and selected with 500 μg/mL geneticin to establish CHO cells continuously-expressing Muc17ct_mIgG2aFc. The continuously-expressing cells were subjected to large-scale cultivation and Muc17ct_mIgG2aFc protein was purified from the culture supernatant. The culture supernatant was applied to HiTrap rProtein A column (GE Healthcare) and, after washing with binding buffer (20 mM sodium phosphate (pH 7.0)), the protein was eluted with elution buffer (0.1 M glycine-HCl (pH 2.7)). The eluate was neutralized by directly transferred to a tube containing neutralizing buffer (1 M Tris-HCl (pH 9.0)). The buffer was replaced with PBS by gel filtration using Superdex 200 HR 26/60 (GE Healthcare). The purified protein was assayed using DC protein assay (BIO-RAD Laboratories, Inc.) and was calculated based on the amount of the standard bovine IgG.

2.3 Construction of Anti-Muc17 Antibodies

Balb/c mice and MRL/MpJUmmCrj-lpr/lpr mice (abbreviated below as MRL/lpr mice, purchased from Charles River Japan) were used as the immunized animals. Immunization was begun at six weeks of age. In the first immunization, Muc17ct_mIgG2aFc of 100 μg/head was emulsified with Freund's complete adjuvant (FCA, Becton, Dickinson and Company) and administered subcutaneously. After two weeks, the antigen of 50 μg/head was emulsified with Freund's incomplete adjuvant (FIA, Becton, Dickinson and Company) and administered subcutaneously. Then from two to five boosting immunizations were given at one week intervals. Four days after the final immunization, pancreas cells were isolated and mixed at 2:1 with P3-X63Ag8U1 mouse myeloma cells (P3U1, purchased from the ATCC), and PEG1500 (Roche Diagnostics) was gradually added for cell fusion. The PEG1500 was diluted by careful addition of RPMI1640 culture medium (GIBCO BRL). PEG1500 was removed by centrifugation, suspended in RPMI1640 containing 10% FBS, and seeded on a 96-well culture plate at 100 µL/well. On the following day, RPMI1640 containing 10% FBS, 1×HAT media supplement (SIGMA), and 0.5×BM-Condimed H1 Hybridoma cloning supplement (Roche Diagnostics) (this medium is referred to hereafter as HAT medium) was added at 100 µL/well. After 2 or 3 days, half of the culture liquid was replaced with HAT medium. After 7 days the culture supernatant was screened by ELISA using Muc17ct_mIgG2aFc immobilized on the plate. The positive clones were monocloned by limit dilution to establish antibodies (MQ016, MQ128, MQ155, MQ169) capable of specifically binding to Muc17. Clones were evaluated using ELISA in which a control Fc fusion protein lacking the Muc17ct sequence is immobilized. The antibody isotype was determined using Isostrip (Roche), and was found to be IgG1 kappa for all antibodies.

Antibody was purified from the culture supernatant of the hybridoma cultured on HAT medium plus FBS (Ultra low IgG) (GIBCO BRL) using HiTrap Protein G HP in the same manner as described above. The buffer of the eluted fraction was replaced with PBS using PD-10 column (Amersham) and was stored at 4° C. The purified antibody was assayed using DC protein assay (BIO-RAD Laboratories, Inc.) and was calculated based on the amount of the standard bovine IgG.

Example 3

Determination of the Anti-Muc17 Antibody Variable Region Nucleotide Sequences

The sequence of the antibody variable region genes was determined for MQ128 and MQ155. The total RNA was extracted from $1 \times 10^7$ hybridoma cells using an RNeasy Plant Mini Kit (QIAGEN).

Using 1 µg total RNA, the 5' terminal gene fragment was amplified using a SMART RACE cDNA Amplification Kit (Clontech Laboratories, Inc.) with the synthetic oligonucleotide MHC-IgG1 (SEQ ID NO:36) complementary to the mouse IgG1 constant region sequence, or with the synthetic oligonucleotide kappa (SEQ ID NO:37) complementary to the mouse κ chain constant region nucleotide sequence. The reverse transcription reaction was carried out for 1 hour and 30 minutes at 42° C. 50 µL PCR solution (containing 5 µL 10× Advantage 2 PCR Buffer, 5 µL 10× Universal Primer A Mix, 0.2 mM dNTPs (dATP, dGTP, dCTP, dTTP), 1 µL Advantage 2 Polymerase Mix (supra, Clontech Laboratories, Inc.), 2.5 µL reverse transcription reaction product, and 10 pmole of the synthetic oligonucleotide MHC-IgG1 or kappa) was subjected to a start temperature of 94° C. for 30 seconds, 5 cycles of 5 seconds/94° C. and 3 minutes/72° C., 5 cycles of 5 seconds/94° C., 10 seconds/70° C., and 3 minutes/72° C., and 25 cycles of 5 seconds/94° C., 10 seconds/68° C., and 3 minutes/72° C. The final reaction product was heated for 7 minutes at 72° C. After purification from agarose gel using a QIAquick Gel Extraction Kit (QIAGEN), each PCR product was cloned into the pGEM-T Easy vector and its nucleotide sequence was determined. For MQ128, the nucleotide sequence of the H chain variable region is shown in SEQ ID NO:18 and its amino acid sequence is shown in SEQ ID NO:19, and the nucleotide sequence of the L chain variable region is shown in SEQ ID NO:20 and its amino acid sequence is shown in SEQ ID NO:21. For MQ155, the nucleotide sequence of the H chain variable region is shown in SEQ ID NO:22 and its amino acid sequence is shown in SEQ ID NO:23, and the nucleotide sequence of the L chain variable region is shown in SEQ ID NO:24 and its amino acid sequence is shown in SEQ ID NO:25.

Example 4

Construction of Anti-Muc17 Mouse-Human Chimeric Antibody

The H chain and L chain variable region sequences of each antibody were ligated to human H chain and human L chain constant regions. For the H chain, PCR was carried out using a synthetic oligonucleotide complementary to the 5' terminal nucleotide sequence of the variable region and containing Kozak sequence and the HindIII site, and a synthetic oligonucleotide complementary to the 3' terminal nucleotide sequence and containing the NheI site. For the L chain, PCR was carried out using a synthetic oligonucleotide complementary to the 5' terminal nucleotide sequence of the variable region and containing Kozak sequence and the BamHI site, and a synthetic oligonucleotide complementary to the 3' terminal side nucleotide sequence and containing the BsiWI site. The resulting PCR products were cloned into the pMCDN_G1k antibody expression plasmid. pMCDN_G1k has a structure in which human IgG1 constant region is cloned into the pMCDN vector and mouse H chain variable region and human H chain (γ1 chain) constant region are connected by the NheI site. In addition, it has a structure in which another expression unit containing the mouse CMV promoter and the human κ chain constant region are inserted and mouse L chain variable region and human L chain (κ chain) constant region are connected by the BsiWI site. In an animal cell the plasmid will express the neomycin resistance gene, the DHFR gene, and the anti-Muc17 mouse-human chimeric antibody gene. The nucleotide sequence of the H chain of the chimeric antibody MQ155 is shown in SEQ ID NO:26 and the amino acid sequence of the H chain of the chimeric antibody MQ155 is shown in SEQ ID NO:27. The nucleotide sequence of the L chain of the chimeric antibodyMQ155 is shown in SEQ ID NO:28 and the amino acid sequence of the L chain of the chimeric antibody MQ155 is shown in SEQ ID NO:29.

pMCDN_G1k_MQ128 and pMCDN_G1k_MQ155 were transfected by electroporation into DG44 cells. CHO cells that continuously expressed the anti-Muc17 chimeric antibody were established by selection with 500 µg/mL geneticin. The antibody was purified from the culture supernatant using HiTrap rProtein A column. The buffer was replaced by PBS with PD-10 column and the purified antibodies (chi.MQ128 (DG), chi.MQ155(DG)) were quantitated using DC protein assay and stored at 4° C.

Example 5

Construction of Low-Fucose Anti-Muc17 Mouse-Human Chimeric Antibody

Modification of the sugar chains on an antibody is known to enhance the ADCC activity of the antibody. For example, WO 99/54342 describes an improvement in the ADCC activity achieved by engineering antibody glycosylation. WO 00/61739 describes modification of the ADCC activity by the presence/absence of fucose in the antibody sugar chains. WO 02/31140 describes the preparation of an antibody having sugar chains lacking α-1,6 core fucose by producing the antibody in YB2/0 cells. WO 2005/017155 describes an example of CHO cells in which the fucose transporter gene has been knocked out (CHO_FTKO). By using similar methodologies, it is possible to produce an antibody having sugar chains lacking α-1,6 core fucose.

The anti-Muc17 mouse-human chimeric antibody expression plasmid constructed as described above was transfected by electroporation into CHO_FTKO cells (WO 2005/017155), and selected with 500 μg/mL geneticin to establish CHO_FTKO cells that continuously expressed the anti-Muc17 chimeric antibody. The antibody was purified from the culture supernatant using HiTrap rProtein A column. The buffer was replaced with PBS with PD-10 column and the purified antibodies (chi.MQ128(FTKO), chi.MQ155 (FTKO)) were quantitated using DC protein assay and stored at 4° C.

Example 6

ELISA Evaluation of the Binding Activity of Anti-Muc17 Antibody

Figure 2:
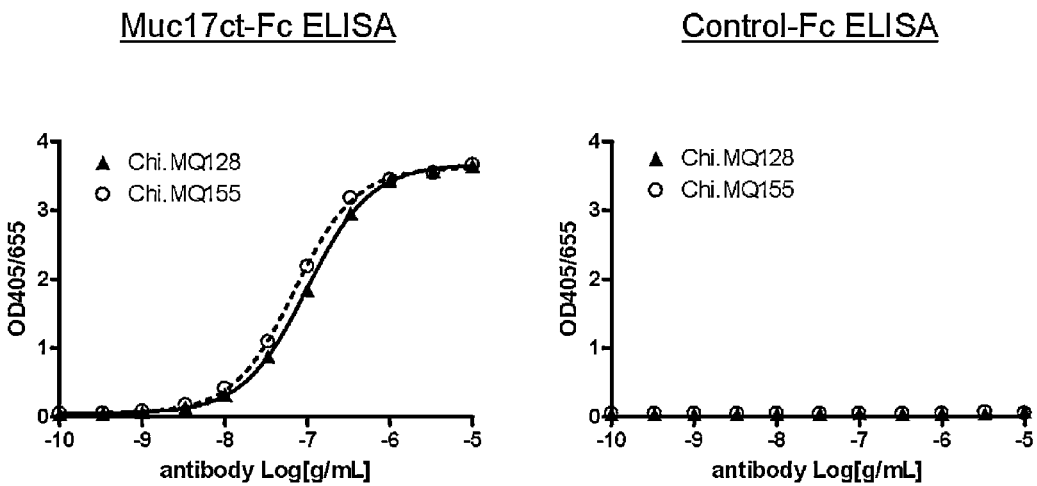
FIG. 2 shows an evaluation by ELISA of the binding activity of a chimeric anti-Muc17 antibody.

Muc17ct_mIgG2aFc protein was diluted with coating buffer (0.1 mol/L $NaHCO_3$ (pH 9.6), 0.02% (w/v) $NaN_3$) to give 1 μg/mL of Muc17ct_mIgG2aFc protein, and added to an immunoplate for overnight at 4° C. for coating. The plate was blocked with dilution buffer (50 mM Tris-HCl (pH 8.1), 1 mM $MgCl_2$, 150 mM NaCl, 0.05% (v/v) Tween20, 0.02% (w/v) $NaN_3$, 1% (w/v) BSA); then the anti-Muc17 antibody was added for 1 hour at room temperature. After washing with rinse buffer (0.05% (v/v) Tween20, PBS), an alkali phosphatase-labeled anti-human κ chain antibody (Sigma, CAT#A3813) was added for 1 hour at room temperature. After washing with rinse buffer, SIGMA104 (Sigma) diluted at 1 mg/mL in the substrate buffer (50 mM $NaHCO_3$ (pH 9.8), 10 mM $MgCl_2$) was added. After color development for 1 hour at room temperature, the absorbance (405 nm, reference 655 nm) was measured using a Benchmark Plus (BIO-RAD Laboratories, Inc.). As shown in FIG. 2, chi.MQ128 and chi.MQ155 exhibited a strong binding activity for Muc17ct_mIgG2aFc in a concentration dependent manner. They did not exhibit binding activity toward the control Fc fusion protein, suggesting that the binding activity is specific to Muc17.

Example 7

Flow Cytometry Evaluation of the Binding Activity of Anti-Muc17 Antibody

Figure 3:
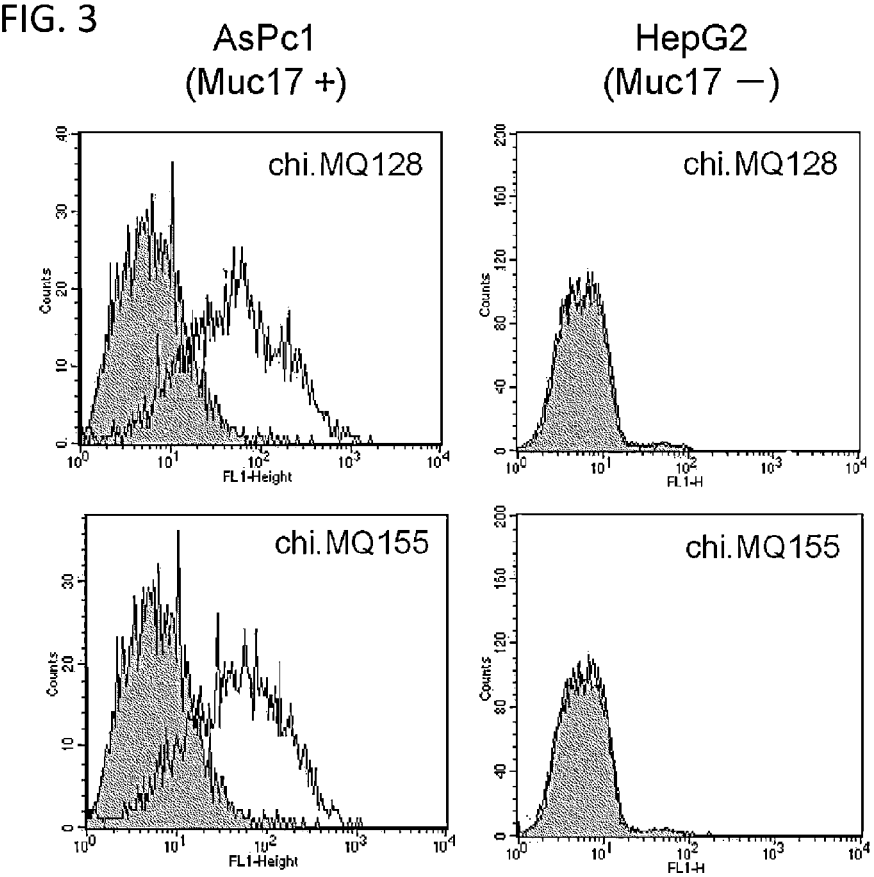
FIG. 3 shows an evaluation by flow cytometry of the binding activity of a chimeric anti-Muc17 antibody.

Binding of the antibodies to a pancreatic cancer cell line AsPc1 was evaluated by flow cytometry. The cells were suspended in FACS buffer (1% FBS/PBS) at $5\times10^5$ cells/mL and dispensed into Multiscreen-HV Filter Plates (Millipore), and the supernatant was removed by centrifugation. Anti-Muc17 antibody diluted to a suitable concentration was added and reacted for 30 minutes on ice. The cells were washed once with FACS buffer. FITC-labeled anti-human IgG antibody was added, and reacted for 30 minutes on ice. Then the supernatant was removed by centrifugation, the cell were suspended in 100 μL FACS buffer and applied to flow cytometry. Flow cytometry was run on FACS Calibur (Becton, Dickinson and Company). The viable cell population was gated with a forward scatter and side scatter histogram. As shown in FIG. 3, chi.MQ128 and chi.MQ155 were strongly bound to the AsPc1 cells. The antibodies did not bind to the non-Muc17-expressing HepG2 cells, suggesting that the binding is specific to Muc17.

Example 8

Measurement of the Antibody-Dependent Cell-Mediated Cytotoxicity (ADCC) of Anti-Muc17 Antibody 8-1) Establishment of Cells that Continuously Express Full Length Human CD16

Full length human CD16 (RefSeq ID, NM_000569) was cloned into the pMCDN mammalian cell expression vector to give pMCDN/CD16. pMCDN/CD16 was transfected by electroporation into NK-92 cells (purchased from the ATCC, CRL-2407), and selected with 500 μg/mL geneticin to establish NK-92 cell line (CD16-NK92) that continuously expressed full length human CD16. The CD16-NK92 cells was cultured in Alpha Minimum Essential Medium (containing L-glutamine, lacking ribonucleotides and deoxyribonucleotides) (Invitrogen Corporation) containing 500 μg/mL geneticin, penicillin/streptomycin (Invitrogen Corporation), 0.2 mM inositol (Sigma), 0.1 mM 2-mercaptoethanol (Invitrogen Corporation), 0.02 mM folic acid (Sigma), 100 U/mL recombinant human interleukin-2 (Peprotech), 10% horse serum (Invitrogen Corporation), and 10% fetal bovine serum (Invitrogen Corporation).

8-2) Measurement of the ADCC Activity of Anti-Muc17 Antibody

50 μL AsPC-1 cells ($8\times10^4$ cells/mL) was added to each well of a 96-well flat-bottom plate and incubated for 2 days at 37° C. in a 5% $CO_2$ incubator. Then 10 μL of a solution containing 240 μCi/mL $^{51}$Cr (Code No. CJS4, GE Healthcare Biosciences Corporation) in RPMI1640 medium containing 10% fetal bovine serum and penicillin/streptomycin (abbreviated as "medium" in the following) was added to each well and incubated for 1 hour. Each well was then washed with 300 μL medium and 100 μL medium was added. 50 μL anti-Muc17 antibody or control human IgG1 antibody (Serotec, Cat. No. PHP010) was added to each well. The final antibody concentration was adjusted by three serial 10-fold dilutions starting from 10 μg/mL. CD16-NK92 cells were suspended in medium at $1\times10^6$ cells/mL and added at 50 μL/well. The plate was incubated for 4 hours at 37° C. in a 5% $CO_2$ incubator, then the radioactivity in 100 μL supernatant was measured using a gamma counter (1480 WIZARD 3", Wallac). The specific chromium release rate was calculated based on the following equation:

$$\text{specific chromium release rate (\%)} = (A-C) \times 100/(B-C)$$

wherein A is the radioactivity (cpm) in each well; B is the average value of the radioactivity (cpm) in wells to which 100 μL of a 2% Nonidet P-40 solution (Code No. 252-23, Nacalai Tesque, Inc.) is added; and C is the average value of the radioactivity (cpm) in wells to which 100 μL medium is added. The test was carried out twice and the average value and standard deviation of the specific chromium release rate were calculated.

Figure 4:
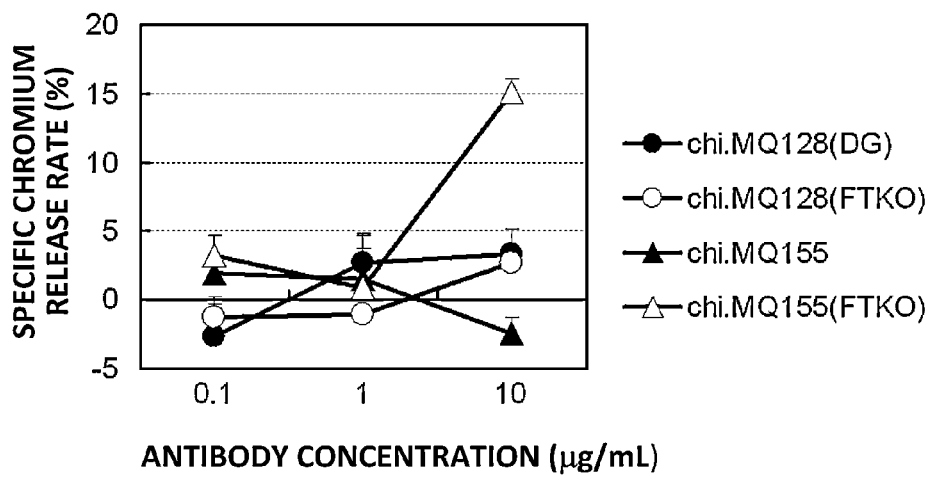
FIG. 4 shows ADCC activity exhibited by the anti-Muc17 antibody on a pancreatic cancer cell line.

The ADCC activity of chi.MQ128(DG), chi.MQ155(DG), chi.MQ128(FTKO), and chi.MQ155(FTKO) was measured and only chi.MQ155(FTKO) exhibited ADCC activity (FIG. 4).

Example 9

Anti-Tumor Effect of Anti-Muc17 Antibody with Hum-ZAP

Figure 5:
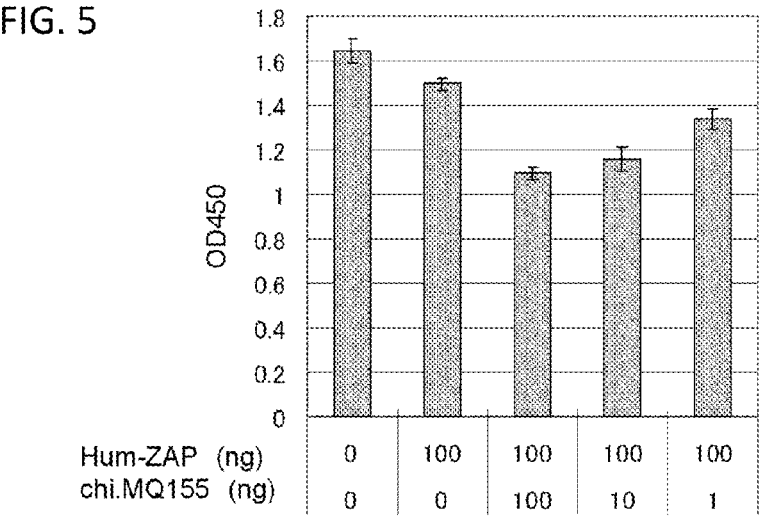
FIG. 5 shows an anti-tumor effect exhibited by the anti-Muc17 antibody with Hum-ZAP.

An immunotoxin targeted to Muc17 was evaluated for its anti-tumor effect using Hum-ZAP. Hum-ZAP (Advanced Targeting Systems) consists of saporin, a protein synthesis-inhibiting toxin, conjugated to an anti-human IgG antibody. Cells of the Muc17-expressing cancer cell line AsPc1 were seeded on a 96-well plate at 2000 cell/100 μL/well on the previous day, and a mixture of 100 ng Hum-ZAP and 0, 1, 10, or 100 ng anti-Muc17 chimeric antibody (chi.MQ155) was added. After incubation for 72 hours, 10 μL Cell Count Reagent SF (Nacalai Tesque, Inc.) was added for another 2 hours, and the absorbance at 450 nm was measured. As shown in FIG. 5, growth inhibition was not seen with Hum-ZAP alone, while an anti-tumor effect was observed for the anti-Muc17 antibody in a concentration dependent manner.

Example 10

Epitope Analysis of the Anti-Muc17 Antibody

Figure 6:
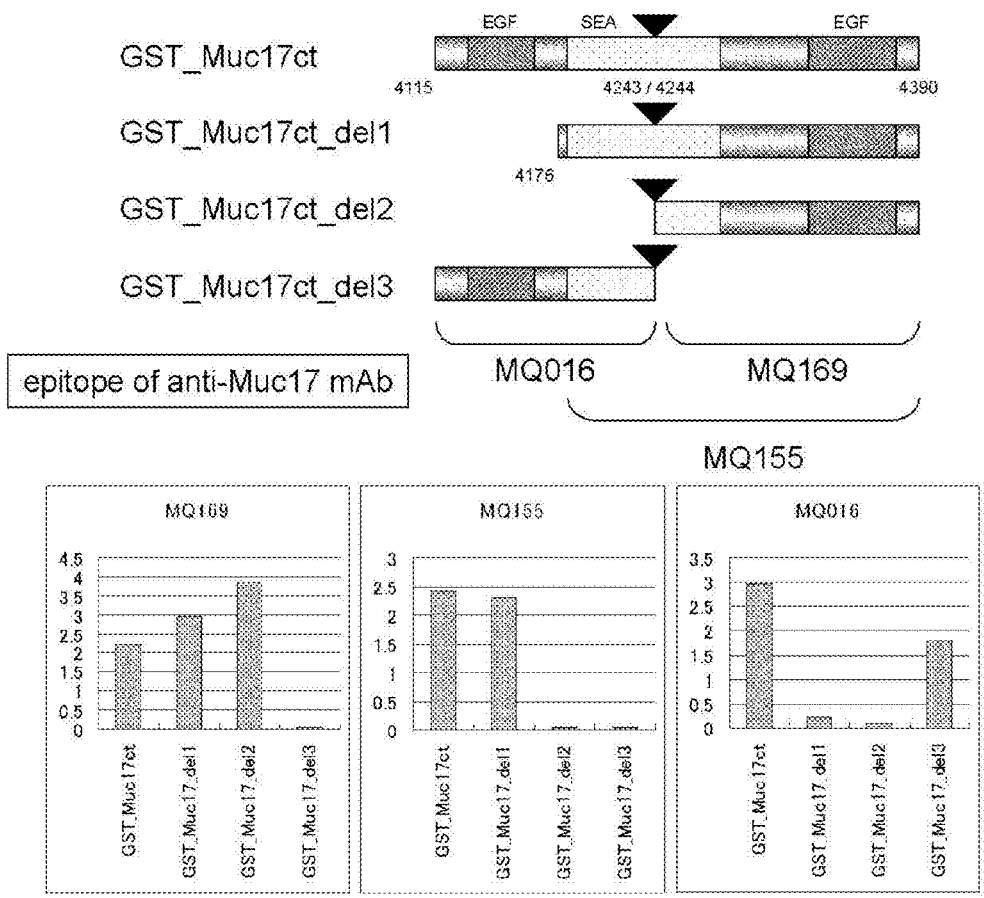
FIG. 6 shows an epitope analysis of anti-Muc17 antibodies.

GST fusion proteins with Muc17 partial sequences were prepared for epitope analysis of the anti-Muc17 antibodies obtained above. PCR amplification was carried out so as to append the EcoRI recognition sequence and the SalI recognition sequence to upstream and downstream of the 4115Thr-4390Leu region of the Muc17 gene, respectively, and cloned into pGEX4T-3 (Takara Bio Inc.). The plasmid was transfected into BL21 to prepare a transformant. The cells were cultured in LB medium, IPTG was added at the concentration of 1 mM during the logarithmic growth phase, and continued cultivation for 4 hours at room temperature. The cells were collected and lysed with B-PER (PIERCE) to prepare inclusion body fraction. It was solubilized with denaturing buffer (8 M urea, 300 mM NaCl, 50 mM Tris-HCl (pH 8.0), 5 mM DTT), and transferred to refolding buffer (50 mM Tris-HCl (pH 8.0), 300 mM NaCl, 1 mM EDTA, 5 mM DTT) for refolding. The solubilized GST fusion protein was affinity purified with Glutathione Sepharose FF column (GE Healthcare). After the buffer was replaced with PBS using PD-10 column (GE Healthcare), the protein was quantified by DC protein assay. The following fusion proteins were prepared according to the same method (FIG. 6): GST_Muc17ct_del1 (4176Ile-4390Leu), GST_Muc17ct_del2 (4244Ser-4390Leu), and GST_Muc17ct_del3 (4115Thr-4243Gly). The purified GST fusion protein was immobilized on an immunoplate at 1 μg/mL. After blocking, anti-Muc17 antibody was added at a concentration of 3 μg/mL, and epitope analysis was carried out by ELISA as described above. MQ155, which exhibited an anti-tumor effect, was strongly bound to GST_Muc17ct and GST_Muc17ct_del1, but did not demonstrate binding activity to GST_Muc17ct_del2 or GST_Muc17ct_del3 (FIG. 6), suggesting that the epitope for MQ155 is located in the region surrounding the predicted cleavage site within the SEA domain. A secreted form of Muc17 is predicted to be present as a splicing variant or by cleavage in the SEA domain. Since MQ155 is predicted to not bind to the secreted-form of Muc17, it is expected that MQ155 will reach the cancer cells without being trapped by the secreted form of Muc17 when administered as a therapeutic antibody. Antibody having such an epitope will be promising as a therapeutic antibody.

The same analysis demonstrated that the epitope for MQ016 is located in the 4115-4243 region and the epitope for MQ169 is located in the 4244-4390 region.

The invention claimed is:

1. An isolated monoclonal antibody recognizing the epitope recognized by an antibody that has a heavy chain variable region having the amino acid sequence set forth in SEQ ID NO:23 and a light-chain variable region having the amino acid sequence set forth in SEQ ID NO:25.

2. An isolated monoclonal antibody that binds to Mucin 17 (Muc17), wherein the antibody has ADCC activity and does not bind to the secreted-form of Muc17, and wherein the antibody comprises a heavy chain variable region that has CDR1 comprising the amino acid sequence set forth in SEQ ID NO:12, CDR 2comprising the amino acid sequence set forth in SEQ ID NO:13, and CDR3 comprising the amino acid sequence set forth in SEQ ID NO:14 and comprises a light chain variable region that has CDR1 comprising the amino acid sequence set forth in SEQ ID NO:15, CDR2 comprising the amino acid sequence set forth in SEQ ID NO:16, and CDR3 comprising the amino acid sequence set forth in SEQ ID NO:17.

3. An isolated monoclonal antibody that binds to Mucin 17 (Muc17), wherein the antibody has ADCC activity and does not bind to the secreted-form of Muc17, which binds to the peptide of SEQ ID NO:3, and which does not bind to the peptide of SEQ ID NO:4 or the peptide of SEQ ID NO:5, and wherein the antibody comprises a heavy chain variable region that has CDR1 comprising the amino acid sequence set forth in SEQ ID NO:12, CDR 2 comprising the amino acid sequence set forth in SEQ ID NO:13, and CDR3 comprising the amino acid sequence set forth in SEQ ID NO:14 and comprises a light chain variable region that has CDR1 comprising the amino acid sequence set forth in SEQ ID NO:15, CDR2 comprising the amino acid sequence set forth in SEQ ID NO:16, and CDR3 comprising the amino acid sequence set forth in SEQ ID NO:17.

4. The antibody according to claim 1, which is a chimeric antibody or a humanized antibody, and which is a low-fucosylated antibody.

5. The antibody according to claim 2, which is a chimeric antibody or a humanized antibody, and which is a low-fucosylated antibody.

* * * * *

UNITED STATES PATENT AND TRADEMARK OFFICE
CERTIFICATE OF CORRECTION

PATENT NO.       : 8,546,546 B2
APPLICATION NO. : 12/667595
DATED            : October 1, 2013
INVENTOR(S)      : Kiyotaka Nakano It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 353 days.

Signed and Sealed this

Fifteenth Day of September, 2015

Michelle K. Lee
*Director of the United States Patent and Trademark Office*

SEQUENCE LISTING

<160> NUMBER OF SEQ ID NOS: 38

<210> SEQ ID NO 1
<211> LENGTH: 14360
<212> TYPE: DNA
<213> ORGANISM: homo sapiens

<400> SEQUENCE: 1

```
tttcgccagc tcctctgggg gtgacaggca agtgagacgt gctcagagct ccgatgccaa      60
ggccagggac catggcgctg tgtctgctga ccttggtcct ctcgctcttg ccccacaag     120 ctgctgcaga acaggacctc agtgtgaaca gggctgtgtg ggatggagga gggtgcatct    180 cccaaggggga cgtcttgaac cgtcagtgcc agcagctgtc tcagcacgtt aggacaggtt    240
ctgcggcaaa caccgccaca ggtacaacat ctacaaatgt cgtggagcca agaatgtatt    300
tgagttgcag caccaaccct gagatgacct cgattgagtc cagtgtgact tcagacactc    360
ctggtgtctc cagtaccagg atgacaccaa cagaatccag aacaacttca gaatctacca    420
gtgacagcac cacacttttc cccagttcta ctgaagacac ttcatctcct acaactcctg    480
aaggcaccga cgtgcccatg tcaacaccaa gtgaagaaag catttcatca acaatggctt    540
ttgtcagcac tgcacctctt cccagttttg aggcctacac atctttaaca tataaggttg    600
atatgagcac acctctgacc acttctactc aggcaagttc atctcctact actcctgaaa    660
gcaccaccat acccaaatca actaacagtg aaggaagcac tccattaaca agtatgcctg    720
ccagcaccat gaaggtggcc agttcagagg ctatcaccct tttgacaact cctgttgaaa    780
tcagcacacc tgtgaccatt tctgctcaag ccagttcatc tcctacaact gctgaaggtc    840
```

```
ccagcctgtc aaactcagct cctagtggag gaagcactcc attaacaaga atgcctctca      900
gcgtgatgct ggtggtcagt tctgaggcta gcacccttc aacaactcct gctgccacca       960
acattcctgt gatcacttct actgaagcca gttcatctcc tacaacggct gaaggcacca    1020
gcataccaac ctcaacttat actgaaggaa gcactccatt aacaagtacg cctgccagca    1080
ccatgccggt tgccacttct gaaatgagca cactttcaat aactcctgtt gacaccagca    1140
cacttgtgac cacttctact gaacccagtt cacttcctac aactgctgaa gctaccagca    1200
tgctaacctc aactcttagt gaaggaagca ctccattaac aaatatgcct gtcagcacca    1260
tattggtggc cagttctgag gctagcacca cttcaacaat tcctgttgac tccaaaactt    1320
ttgtgaccac tgctagtgaa gccagctcat ctcccacaac tgctgaagat accagcattg    1380
caacctcaac tcctagtgaa ggaagcactc cattaacaag tatgcctgtc agcaccactc    1440
cagtggccag ttctgaggct agcaaccttt caacaactcc tgttgactcc aaaactcagg    1500
tgaccacttc tactgaagcc agttcatctc ctccaactgc tgaagttaac agcatgccaa    1560
cctcaactcc tagtgaagga agcactccat taacaagtat gtctgtcagc accatgccgg    1620
tggccagttc tgaggctagc acccttcaa caactcctgt tgacaccagc acacctgtga    1680
ccacttctag tgaagccagt tcatcttcta caactcctga aggtaccagc ataccaacct    1740
caactcctag tgaaggaagc actccattaa caaacatgcc tgtcagcacc aggctggtgg    1800
tcagttctga ggctagcacc acttcaacaa ctcctgctga ctccaacact tttgtgacca    1860
cttctagtga agctagttca tcttctacaa ctgctgaagg taccagcatg ccaacctcaa    1920
cttacagtga aagaggcact acaataacaa gtatgtctgt cagcaccaca ctggtggcca    1980
gttctgaggc tagcaccctt tcaacaactc ctgttgactc caacactcct gtgaccactt    2040
caactgaagc cacttcatct tctacaactg cggaaggtac cagcatgcca acctcaactt    2100
atactgaagg aagcactcca ttaacaagta tgcctgtcaa caccacactg gtggccagtt    2160
ctgaggctag cacccttca acaactcctg ttgacaccag cacacctgtg accacttcaa    2220
ctgaagccag ttcctctcct acaactgctg atggtgccag tatgccaacc tcaactccta    2280
gtgaaggaag cactccatta acaagtatgc ctgtcagcaa aacgctgttg accagttctg    2340
aggctagcac ccttcaaca actcctcttg acacaagcac acatatcacc acttctactg    2400
aagccagttg ctctcctaca accactgaag gtaccagcat gccaatctca actcctagtg    2460
aaggaagtcc tttattaaca agtatacctg tcagcatcac accggtgacc agtcctgagg    2520
ctagcaccct ttcaacaact cctgttgact ccaacagtcc tgtgaccact tctactgaag    2580
tcagttcatc tcctacacct gctgaaggta ccagcatgcc aacctcaact tatagtgaag    2640
gaagaactcc tttaacaagt atgcctgtca gcaccacact ggtggccact tctgcaatca    2700 gcacccttc aacaactcct gttgacacca gcacacctgt gaccaattct actgaagccc    2760
gttcgtctcc tacaacttct gaaggtacca gcatgccaac ctcaactcct ggggaaggaa    2820
gcactccatt aacaagtatg cctgacagca ccacgccggt agtcagttct gaggctagaa    2880
cactttcagc aactcctgtt gacaccagca cacctgtgac cacttctact gaagccactt    2940
catctcctac aactgctgaa ggtaccagca taccaacctc gactcctagt gaaggaacga    3000
ctccattaac aagcacacct gtcagccaca cgctggtggc caattctgag gctagcaccc    3060
tttcaacaac tcctgttgac tccaacactc ctttgaccac ttctactgaa gccagttcac    3120
ctcctcccac tgctgaaggt accagcatgc caacctcaac tcctagtgaa ggaagcactc    3180
cattaacacg tatgcctgtc agcaccacaa tggtggccag ttctgaaacg agcacacttt    3240
```

```
caacaactcc tgctgacacc agcacacctg tgaccactta ttctcaagcc agttcatctt   3300
ctacaactgc tgacggtacc agcatgccaa cctcaactta tagtgaagga agcactccac   3360
taacaagtgt gcctgtcagc accaggctgg tggtcagttc tgaggctagc acccttttca   3420
caactcctgt cgacaccagc atacctgtca ccacttctac tgaagccagt tcatctccta   3480
caactgctga aggtaccagc ataccaacct cacctcccag tgaaggaacc actccgttag   3540
caagtatgcc tgtcagcacc acgctggtgg tcagttctga ggctaacacc ctttcaacaa   3600
ctcctgtgga ctccaaaact caggtggcca cttctactga agccagttca cctcctccaa   3660
ctgctgaagt taccagcatg ccaacctcaa ctcctggaga agaagcact ccattaacaa   3720 gtatgcctgt cagacacacg ccagtggcca gttctgaggc tagcacccct tcaacatctc   3780
ccgttgacac cagcacacct gtgaccactt ctgctgaaac cagttcctct cctacaaccg   3840
ctgaaggtac cagcttgcca acctcaacta ctagtgaagg aagtactcta ttaacaagta   3900
tacctgtcag caccacgctg gtgaccagtc ctgaggctag caccctttta caactcctg   3960 ttgacactaa aggtcctgtg gtcacttcta atgaagtcag ttcatctcct acacctgctg   4020
aaggtaccag catgccaacc tcaacttata gtgaaggaag aactcccttta caagtatac   4080 ctgtcaacac cacactggtg gccagttctg caatcagcat cctttcaaca actcctgttg   4140
acaacagcac acctgtgacc acttctactg aagcctgttc atctcctaca acttctgaag   4200
gtaccagcat gccaaactca atcctagtg aaggaaccac tccgttaaca agtatacctg   4260
tcagcaccac gccggtagtc agttctgagg ctagcacccct ttcagcaact cctgttgaca   4320
ccagcacccc tgggaccact tctgctgaag ccacttcatc tcctacaact gctgaaggta   4380
tcagcatacc aacctcaact cctagtgaag gaaagactcc attaaaaagt ataaccgtca   4440
gcaacacgcc ggtggccaat tctgaggcta gcaccctttc aacaactcct gttgactcta   4500
acagtcctgt ggtcacttct acagcagtca gttcatctcc tacacctgct gaaggtacca   4560
gcatagcaat ctcaacgcct agtgaaggaa gcactgcatt aacaagtata cctgtcagca   4620
ccacaacagt ggccagttct gaaatcaaca gcctttcaac aactcctgct gtcaccagca   4680
cacctgtgac cacttattct caagccagtt catctcctac aactgctgac ggtaccagca   4740
tgcaaacctc aacttatagt gaaggaagca ctccactaac aagtttgcct gtcagcacca   4800
tgctggtggt cagttctgag gctaacaccc tttcaacaac ccctattgac tccaaaactc   4860
aggtgaccgc ttctactgaa gccagttcat ctacaaccgc tgaaggtagc agcatgacaa   4920
tctcaactcc tagtgaagga agtcctctat taacaagtat acctgtcagc accacgccgg   4980
tggccagtcc tgaggctagc acccttttca caactcctgt tgactccaac agtcctgtga   5040
tcacttctac tgaagtcagt tcatctccta cacctgctga aggtaccagc atgccaacct   5100
caacttatac tgaaggaaga actccttta caagtataac tgtcagaaca caccggtgg   5160 ccagctctgc aatcagcacc ctttcaacaa ctcccgttga acagcacaca cctgtgacca   5220
cttctactga agcccgttca tctcctacaa cttctgaagg taccagcatg ccaaactcaa   5280
ctcctagtga aggaaccact ccattaacaa gtatacctgt cagcaccacg ccggtactca   5340
gttctgaggc tagcacccct tcagcaactc ctattgacac cagcaccct gtgaccactt   5400 ctactgaagc cacttcgtct cctacaactg ctgaaggtac cagcatacca acctcgactc   5460
ttagtgaagg aatgactcca ttaacaagca cacctgtcag ccacacgctg gtggccaatt   5520
ctgaggctag cacccttca acaactcctg ttgactctaa cagtcctgtg gtcacttcta   5580
cagcagtcag ttcatctcct acacctgctg aaggtaccag catagcaacc tcaacgccta   5640
```

```
gtgaaggaag cactgcatta acaagtatac ctgtcagcac cacaacagtg gccagttctg   5700
aaaccaacac cctttcaaca actcccgctg tcaccagcac acctgtgacc acttatgctc   5760
aagtcagttc atctcctaca actgctgacg gtagcagcat gccaacctca actcctaggg   5820
aaggaaggcc tccattaaca agtatacctg tcagcaccac aacagtggcc agttctgaaa   5880
tcaacaccct ttcaacaact cttgctgaca ccaggacacc tgtgaccact tattctcaag   5940
ccagttcatc tcctacaact gctgatggta ccagcatgcc aacccagct tatagtgaag    6000 gaagcactcc actaacaagt atgcctctca gcaccacgct ggtggtcagt tctgaggcta   6060
gcactctttc cacaactcct gttgacacca gcactcctgc caccacttct actgaaggca   6120
gttcatctcc tacaactgca ggaggtacca gcatacaaac ctcaactcct agtgaacgga   6180
ccactccatt agcaggtatg cctgtcagca ctacgcttgt ggtcagttct gagggtaaca   6240
ccctttcaac aactcctgtt gactccaaaa ctcaggtgac caattctact gaagccagtt   6300
catctgcaac cgctgaaggt agcagcatga caatctcagc tcctagtgaa ggaagtcctc   6360
tactaacaag tatacctctc agcaccacgc cggtggccag tcctgaggct agcacccttt   6420
caacaactcc tgttgactcc aacagtcctg tgatcacttc tactgaagtc agttcatctc   6480
ctatacctac tgaaggtacc agcatgcaaa cctcaactta tagtgacaga agaactcctt   6540
taacaagtat gcctgtcagc accacagtgg tggccagttc tgcaatcagc acccttttcaa 6600 caactcctgt tgacaccagc acctgtga ccaattctac tgaagcccgt tcatctccta    6660
caacttctga aggtaccagc atgccaacct caactcctag tgaaggaagc actccattca   6720
caagtatgcc tgtcagcacc atgccggtag ttacttctga ggctagcacc ctttcagcaa   6780
ctcctgttga caccagcaca cctgtgacca cttctactga agccacttca tctcctacaa   6840
ctgctgaagg taccagcata ccaacttcaa ctcttagtga aggaacgact ccattaacaa   6900
gtatacctgt cagccacacg ctggtggcca attctgaggt tagcaccctt tcaacaactc   6960
ctgttgactc caacactcct ttcactactt ctactgaagc cagttcacct cctcccactg   7020
ctgaaggtac cagcatgcca acctcaactt ctagtgaagg aaacactcca ttaacacgta   7080
tgcctgtcag caccacaatg gtggccagtt ttgaaacaag cacactttct acaactcctg   7140
ctgacaccag cacacctgtg actacttatt ctcaagccgg ttcatctcct acaactgctg   7200
acgatactag catgccaacc tcaacttata gtgaaggaag cactccacta acaagtgtgc   7260
ctgtcagcac catgccggtg gtcagttctg aggctagcac ccattccaca actcctgttg   7320
acaccagcac acctgtcacc acttctactg aagccagttc atctcctaca actgctgaag   7380
gtaccagcat accaacctca cctcctagtg aaggaaccac tccgttagca agtatgcctg   7440
tcagcaccac gccggtggtc agttctgagg ctggcacccct ttccacaact cctgttgaca   7500
ccagcacacc tatgaccact tctactgaag ccagttcatc tcctacaact gctgaagata   7560
tcgtcgtgcc aatctcaact gctagtgaag gaagtactct attaacaagt atacctgtca   7620
gcaccacgcc agtggccagt cctgaggcta gcacccttt aacaactcct gttgactcca    7680
acagtcctgt ggtcacttct actgaaatca gttcatctgc tacatccgct gaaggtacca   7740
gcatgcctac ctcaacttat agtgaaggaa gcactccatt aagaagtatg cctgtcagca   7800
ccaagccgtt ggccagttct gaggctagca ctctttcaac aactcctgtt gacaccagca   7860
tacctgtcac cacttctact gaaaccagtt catctcctac aactgcaaaa gataccagca   7920
tgccaatctc aactcctagt gaagtaagta cttcattaac aagtatactt gtcagccaca   7980
tgccagtggc cagttctgag gctagcaccc tttcaacaac tcctgttgac accaggacac   8040
```

```
ttgtgaccac ttccactgga accagttcat ctcctacaac tgctgaaggt agcagcatgc    8100
caacctcaac tcctggtgaa agaagcactc cattaacaaa tatacttgtc agcaccacgc    8160
tgttggccaa ttctgaggct agcacccttt caacaactcc tgttgacacc agcacacctg    8220
tcaccacttc tgctgaagcc agttcttctc ctacaactgc tgaaggtacc agcatgcgaa    8280
tctcaactcc tagtgatgga agtactccat taacaagtat acttgtcagc accctgccag    8340
tggccagttc tgaggctagc accgtttcaa caactgctgt tgacaccagc atacctgtca    8400
ccacttctac tgaagccagt tcctctccta caactgctga agttaccagc atgccaacct    8460
caactcctag tgaaacaagt actccattaa ctagtatgcc tgtcaaccac acgccagtgg    8520
ccagttctga ggctggcacc ctttcaacaa ctcctgttga caccagcaca cctgtgacca    8580
cttctactaa agccagttca tctcctacaa ctgctgaagg tatcgtcgtg ccaatctcaa    8640
ctgctagtga aggaagtact ctattaacaa gtatacctgt cagcaccacg ccggtggcca    8700
gttctgaggc tagcacccct tcaacaactc ctgttgatac cagcatacct gtcaccactt    8760
ctactgaagg cagttcttct cctacaactg ctgaaggtac cagcatgcca atctcaactc    8820
ctagtgaagt aagtactcca ttaacaagta tacttgtcag caccgtgcca gtggccggtt    8880
ctgaggctag caccctttca caactcctg ttgacaccag gacacctgtc accacttctg    8940
ctgaagctag ttcttctcct acaactgctg aaggtaccag catgccaatc tcaactcctg    9000
gcgaaagaag aactccatta acaagtatgt ctgtcagcac catgccggtg ccagttctg    9060 aggctagcac ccttttcaaga actcctgctg acaccagcac acctgtgacc acttctactg    9120
aagccagttc ctctcctaca actgctgaag gtaccggcat accaatctca actcctagtg    9180
aaggaagtac tccattaaca agtatacctg tcagcaccac gccagtggcc attcctgagg    9240 ctagcacccct ttcaacaact cctgttgact ccaacagtcc tgtggtcact tctactgaag    9300
tcagttcatc tcctacacct gctgaaggta ccagcatgcc aatctcaact tatagtgaag    9360
gaagcactcc attaacaggt gtgcctgtca gcaccacacc ggtgaccagt tctgcaatca    9420
gcaccctttc aacaactcct gttgacacca gcacacctgt gaccacttct actgaagccc    9480
attcatctcc tacaacttct gaaggtacca gcatgccaac ctcaactcct agtgaaggaa    9540
gtactccatt aacatatatg cctgtcagca ccatgctggt agtcagttct gaggatagca    9600
ccctttcagc aactcctgtt gacaccagca cacctgtgac cacttctact gaagccactt    9660
catctacaac tgctgaaggt accagcattc aacctcaac tcctagtgaa ggaatgactc    9720
cattaactag tgtacctgtc agcaacacgc cggtggccag ttctgaggct agcatccttt    9780
caacaactcc tgttgactcc aacactcctt tgaccacttc tactgaagcc agttcatctc    9840 ctccactgc tgaaggtacc agcatgccaa cctcaactcc tagtgaagga agcactccat    9900
taacaagtat gcctgtcagc accacaacgg tggccagttc tgaaacgagc cccttttcaa    9960
caactcctgc tgacaccagc acacctgtga ccacttattc tcaagccagt tcatctcctc    10020
caattgctga cggtactagc atgccaacct caacttatag tgaaggaagc actccactaa    10080
caaatatgtc tttcagcacc acgccagtgg tcagttctga ggctagcacc ctttccacaa    10140
ctcctgttga caccagcaca cctgtcacca cttctactga agccagttta tctcctacaa    10200
ctgctgaagg taccagcata ccaacctcaa gtcctagtga aggaaccact ccattagcaa    10260
gtatgcctgt cagcaccacg ccggtggtca gttctgaggt taacaccctt tcaacaactc    10320
ctgtggactc caacactctg gtgaccactt tactgaagc cagttcatct cctacaatcg    10380
ctgaaggtac cagcttgcca acctcaacta ctagtgaagg aagcactcca ttatcaatta    10440
```

```
tgcctctcag taccacgccg gtggccagtt ctgaggctag caccctttca acaactcctg   10500
ttgacaccag cacacctgtg accacttctt ctccaaccaa ttcatctcct acaactgctg   10560
aagttaccag catgccaaca tcaactgctg gtgaaggaag cactccatta acaaatatgc   10620
ctgtcagcac cacaccggtg gccagttctg aggctagcac cctttcaaca actcctgttg   10680
actccaacac ttttgttacc agttctagtc aagccagttc atctccagca actcttcagg   10740
tcaccactat gcgtatgtct actccaagtg aaggaagctc ttcattaaca actatgctcc   10800
tcagcagcac atatgtgacc agttctgagg ctagcacacc ttccactcct tctgttgaca   10860
gaagcacacc tgtgaccact tctactcaga gcaattctac tcctcacctt cctgaagtta   10920
tcaccctgcc aatgtcaact cctagtgaag taagcactcc attaaccatt atgcctgtca   10980
gcaccacatc ggtgaccatt tctgaggctg gcacagcttc aacacttcct gttgacacca   11040
gcacacctgt gatcacttct acccaagtca gttcatctcc tgtgactcct gaaggtacca   11100
ccatgccaat ctgacgcct agtgaaggaa gcactccatt aacaactatg cctgtcagca   11160
ccacacgtgt gaccagctct gagggtagca cccctttcaac accttctgtt gtcaccagca   11220
cacctgtgac cacttctact gaagccattt catcttctgc aactcttgac agcaccacca   11280
tgtctgtgtc aatgcccatg gaaataagca cccttgggac cactattctt gtcagtacca   11340
cacctgttac gaggtttcct gagagtagca ccccttccat accatctgtt tacaccagca   11400
tgtctatgac cactgcctct gaaggcagtt catctcctac aactcttgaa ggcaccacca   11460
ccatgcctat gtcaactacg agtgaaagaa gcactttatt gacaactgtc ctcatcagcc   11520
ctatatctgt gatgagtcct tctgaggcca gcacactttc aacacctcct ggtgatacca   11580
gcacaccttt gctcacctct accaaagccg gttcattctc catacctgct gaagtcacta   11640
ccatacgtat ttcaattacc agtgaaagaa gcactccatt aacaactctc cttgtcagca   11700
ccacacttcc aactagcttt cctgggccca gcatagcttc gacacctcct cttgacacaa   11760
gcacaacttt taccccttct actgacactg cctcaactcc cacaattcct gtagccacca   11820
ccatatctgt atcagtgatc acagaaggaa gcacacctgg gacaaccatt tttattccca   11880
gcactcctgt caccagttct actgctgatg tcttttcctgc aacaactggt gctgtatcta   11940
cccctgtgat aacttccact gaactaaaca caccatcaac ctccagtagt agtaccacca   12000
catctttttc aactactaag gaattttacaa caccgcaat gactactgca gctcccctca   12060
catatgtgac catgtctact gcccccagca cacccagaac aaccagcaga ggctgcacta   12120
cttctgcatc aacgctttct gcaaccagta cacctcacac ctctacttct gtcaccaccc   12180
gtcctgtgac cccttcatca gaatccagca ggccgtcaac aattacttct cacaccatcc   12240
cacctacatt tcctcctgct cactccagta cacctccaac aacctctgcc tcctccacga   12300
ctgtgaaccc tgaggctgtc accaccatga ccaccaggac aaaacccagc acacggacca   12360
cttccttccc cacggtgacc accaccgctg tccccacgaa tactacaatt aagagcaacc   12420
ccacctcaac tcctactgtg ccaagaacca caacatgctt tggagatggg tgccagaata   12480
cggcctctcg ctgcaagaat ggaggcacct gggatgggct caagtgccag tgtcccaacc   12540
tctattatgg ggagttgtgt gaggaggtgg tcagcagcat tgacataggg ccaccggaga   12600
ctatctctgc ccaaatggaa ctgactgtga cagtgaccag tgtgaagttc accgaagagc   12660
taaaaaacca ctcttcccag gaattccagg agttcaaaca gacattcacg gaacagatga   12720
atattgtgta ttccgggatc cctgagtatg tcggggtgaa catcacaaag ctacgtcttg   12780
gcagtgtggt ggtggagcat gacgtcctcc taagaaccaa gtacacacca gaatacaaga   12840
```

```
cagtattgga caatgccacc gaagtagtga aagagaaaat cacaaaagtg accacacagc    12900
aaataatgat taatgatatt tgctcagaca tgatgtgttt caacaccact ggcacccaag    12960
tgcaaaacat tacggtgacc cagtacgacc ctgaagagga ctgccggaag atggccaagg    13020
aatatggaga ctacttcgta gtggagtacc gggaccagaa gccatactgc atcagcccct    13080
gtgagcctgg cttcagtgtc tccaagaact gtaacctcgg caagtgccag atgtctctaa    13140
gtggacctca gtgcctctgc gtgaccacgg aaactcactg gtacagtggg gagacctgta    13200
accagggcac ccagaagagt ctggtgtacg gcctcgtggg ggcaggggtc gtgctgatgc    13260
tgatcatcct ggtagctctc ctgatgctcg ttttccgctc caagagagag gtgaaacggc    13320
aaaagtacag attgtctcag ttatacaagt ggcaagaaga ggacagtgga ccagctcctg    13380
ggaccttcca aaacattggc tttgacatct gccaagatga tgattccatc cacctggagt    13440
ccatctatag taatttccag ccctccttga gacacataga ccctgaaaca aagatccgaa    13500
ttcagaggcc tcaggtaatg acgacatcat tttaaggcat ggagctgaga agtctgggag    13560
tgaggagatc ccagtccggc taagcttggt ggagcatttt cccattgaga gccttccatg    13620
ggaactcaat gttcccattg taagtacagg aaacaagccc tgtacttacc aaggagaaag    13680
aggagagaca gcagtgctgg gagattctca aatagaaacc cgtggacgct ccaatgggct    13740
tgtcatgata tcaggctagg ctttcctgct cattttcaa agacgctcca gatttgaggg    13800
tactctgact gcaacatctt tcaccccatt gatcgccagg attgatttgg ttgatctggc    13860
tgagcaggcg ggtgtccccg tcctcccctca ctgccccata tgtgtccctc ctaaagctgc    13920
atgctcagtt gaagaggacg agaggacgac cttctctgat agaggaggac cacgcttcag    13980
tcaaaggcat acaagtatct atctggactt ccctgctagc acttccaaac aagctcagag    14040
atgttcctcc cctcatctgc ccgggttcag taccatggac agcgccctcg acccgctgtt    14100
tacaaccatg accccttgga cactggactg catgcacttt acatatcaca aaatgctctc    14160
ataagaatta ttgcatacca tcttcatgaa aaacacctgt atttaaatat agagcattta    14220
ccttttggta tataagattg tgggtatttt ttaagttctt attgttatga gttctgatttt    14280 tttccttagt aaatattata atatatattt gtagtaacta aaaataataa agcaatttta    14340 ttacaattt aaaaaaaaaa                                                 14360
```

<210> SEQ ID NO 2
<211> LENGTH: 4493
<212> TYPE: PRT
<213> ORGANISM: homo sapiens

<400> SEQUENCE: 2

Met Pro Arg Pro Gly Thr Met Ala Leu Cys Leu Leu Thr Leu Val Leu
1               5                   10                  15

Ser Leu Leu Pro Pro Gln Ala Ala Ala Glu Gln Asp Leu Ser Val Asn
            20                  25                  30

Arg Ala Val Trp Asp Gly Gly Gly Cys Ile Ser Gln Gly Asp Val Leu
        35                  40                  45

Asn Arg Gln Cys Gln Gln Leu Ser Gln His Val Arg Thr Gly Ser Ala
    50                  55                  60

Ala Asn Thr Ala Thr Gly Thr Thr Ser Thr Asn Val Val Glu Pro Arg
65                  70                  75                  80

Met Tyr Leu Ser Cys Ser Thr Asn Pro Glu Met Thr Ser Ile Glu Ser
                85                  90                  95

Ser Val Thr Ser Asp Thr Pro Gly Val Ser Ser Thr Arg Met Thr Pro
            100                 105                 110

```
Thr Glu Ser Arg Thr Thr Ser Glu Ser Thr Ser Asp Ser Thr Thr Leu
            115                 120                 125
Phe Pro Ser Ser Thr Glu Asp Thr Ser Ser Pro Thr Thr Pro Glu Gly
            130                 135                 140
Thr Asp Val Pro Met Ser Thr Pro Ser Glu Glu Ser Ile Ser Ser Thr
145                 150                 155                 160
Met Ala Phe Val Ser Thr Ala Pro Leu Pro Ser Phe Glu Ala Tyr Thr
                165                 170                 175
Ser Leu Thr Tyr Lys Val Asp Met Ser Thr Pro Leu Thr Thr Ser Thr
                180                 185                 190
Gln Ala Ser Ser Ser Pro Thr Thr Pro Glu Ser Thr Thr Ile Pro Lys
            195                 200                 205
Ser Thr Asn Ser Glu Gly Ser Thr Pro Leu Thr Ser Met Pro Ala Ser
            210                 215                 220
Thr Met Lys Val Ala Ser Ser Glu Ala Ile Thr Leu Leu Thr Thr Pro
225                 230                 235                 240
Val Glu Ile Ser Thr Pro Val Thr Ile Ser Ala Gln Ala Ser Ser Ser
                245                 250                 255
Pro Thr Thr Ala Glu Gly Pro Ser Leu Ser Asn Ser Ala Pro Ser Gly
            260                 265                 270
Gly Ser Thr Pro Leu Thr Arg Met Pro Leu Ser Val Met Leu Val Val
            275                 280                 285
Ser Ser Glu Ala Ser Thr Leu Ser Thr Thr Pro Ala Ala Thr Asn Ile
            290                 295                 300
Pro Val Ile Thr Ser Thr Glu Ala Ser Ser Pro Thr Thr Ala Glu
305                 310                 315                 320
Gly Thr Ser Ile Pro Thr Ser Thr Tyr Thr Glu Gly Ser Thr Pro Leu
                325                 330                 335
Thr Ser Thr Pro Ala Ser Thr Met Pro Val Ala Thr Ser Glu Met Ser
            340                 345                 350
Thr Leu Ser Ile Thr Pro Val Asp Thr Ser Thr Leu Val Thr Thr Ser
            355                 360                 365
Thr Glu Pro Ser Ser Leu Pro Thr Thr Ala Glu Ala Thr Ser Met Leu
            370                 375                 380
Thr Ser Thr Leu Ser Glu Gly Ser Thr Pro Leu Thr Asn Met Pro Val
385                 390                 395                 400
Ser Thr Ile Leu Val Ala Ser Ser Glu Ala Ser Thr Thr Ser Thr Ile
                405                 410                 415
Pro Val Asp Ser Lys Thr Phe Val Thr Thr Ala Ser Glu Ala Ser Ser
                420                 425                 430
Ser Pro Thr Thr Ala Glu Asp Thr Ser Ile Ala Thr Ser Thr Pro Ser
            435                 440                 445
Glu Gly Ser Thr Pro Leu Thr Ser Met Pro Val Ser Thr Thr Pro Val
            450                 455                 460
Ala Ser Ser Glu Ala Ser Asn Leu Ser Thr Thr Pro Val Asp Ser Lys
465                 470                 475                 480
Thr Gln Val Thr Thr Ser Thr Glu Ala Ser Ser Pro Thr Ala
                485                 490                 495
Glu Val Asn Ser Met Pro Thr Ser Thr Pro Ser Glu Gly Ser Thr Pro
                500                 505                 510
Leu Thr Ser Met Ser Val Ser Thr Met Pro Val Ala Ser Ser Glu Ala
                515                 520                 525
Ser Thr Leu Ser Thr Thr Pro Val Asp Thr Ser Thr Pro Val Thr Thr
```

```
                530                 535                 540
Ser Ser Glu Ala Ser Ser Ser Thr Thr Pro Glu Gly Thr Ser Ile
545                 550                 555                 560

Pro Thr Ser Thr Pro Ser Glu Gly Ser Thr Pro Leu Thr Asn Met Pro
                565                 570                 575

Val Ser Thr Arg Leu Val Val Ser Ser Glu Ala Ser Thr Thr Ser Thr
                580                 585                 590

Thr Pro Ala Asp Ser Asn Thr Phe Val Thr Thr Ser Glu Ala Ser
                595                 600                 605

Ser Ser Ser Thr Thr Ala Glu Gly Thr Ser Met Pro Thr Ser Thr Tyr
                610                 615                 620

Ser Glu Arg Gly Thr Thr Ile Thr Ser Met Ser Val Ser Thr Thr Leu
625                 630                 635                 640

Val Ala Ser Ser Glu Ala Ser Thr Leu Ser Thr Thr Pro Val Asp Ser
                    645                 650                 655

Asn Thr Pro Val Thr Thr Ser Glu Ala Thr Ser Ser Thr Thr
                660                 665                 670

Ala Glu Gly Thr Ser Met Pro Thr Ser Thr Tyr Thr Glu Gly Ser Thr
                675                 680                 685

Pro Leu Thr Ser Met Pro Val Asn Thr Thr Leu Val Ala Ser Ser Glu
690                 695                 700

Ala Ser Thr Leu Ser Thr Thr Pro Val Asp Thr Ser Thr Pro Val Thr
705                 710                 715                 720

Thr Ser Thr Glu Ala Ser Ser Pro Thr Thr Ala Asp Gly Ala Ser
                    725                 730                 735

Met Pro Thr Ser Thr Pro Ser Glu Gly Ser Thr Pro Leu Thr Ser Met
                740                 745                 750

Pro Val Ser Lys Thr Leu Leu Thr Ser Glu Ala Ser Thr Leu Ser
                755                 760                 765

Thr Thr Pro Leu Asp Thr Ser Thr His Ile Thr Thr Ser Thr Glu Ala
770                 775                 780

Ser Cys Ser Pro Thr Thr Thr Glu Gly Thr Ser Met Pro Ile Ser Thr
785                 790                 795                 800

Pro Ser Glu Gly Ser Pro Leu Leu Thr Ser Ile Pro Val Ser Ile Thr
                805                 810                 815

Pro Val Thr Ser Pro Glu Ala Ser Thr Leu Ser Thr Thr Pro Val Asp
                820                 825                 830

Ser Asn Ser Pro Val Thr Thr Ser Thr Glu Val Ser Ser Ser Pro Thr
                835                 840                 845

Pro Ala Glu Gly Thr Ser Met Pro Thr Ser Thr Tyr Ser Glu Gly Arg
850                 855                 860

Thr Pro Leu Thr Ser Met Pro Val Ser Thr Thr Leu Val Ala Thr Ser
865                 870                 875                 880

Ala Ile Ser Thr Leu Ser Thr Thr Pro Val Asp Thr Ser Thr Pro Val
                    885                 890                 895

Thr Asn Ser Thr Glu Ala Arg Ser Ser Pro Thr Thr Ser Glu Gly Thr
                900                 905                 910

Ser Met Pro Thr Ser Thr Pro Gly Glu Gly Ser Thr Pro Leu Thr Ser
                915                 920                 925

Met Pro Asp Ser Thr Thr Pro Val Val Ser Ser Glu Ala Arg Thr Leu
                930                 935                 940

Ser Ala Thr Pro Val Asp Thr Ser Thr Pro Val Thr Ser Thr Glu
945                 950                 955                 960
```

-continued

```
Ala Thr Ser Ser Pro Thr Thr Ala Glu Gly Thr Ser Ile Pro Thr Ser
                965                 970                 975

Thr Pro Ser Glu Gly Thr Thr Pro Leu Thr Ser Thr Pro Val Ser His
                980                 985                 990

Thr Leu Val Ala Asn Ser Glu Ala Ser Thr Leu Ser Thr Thr Pro Val
                995                1000                1005

Asp Ser Asn Thr Pro Leu Thr Ser Thr Glu Ala Ser Ser Pro
       1010                1015                1020

Pro Pro Thr Ala Glu Gly Thr Ser Met Pro Thr Ser Thr Pro Ser
       1025                1030                1035

Glu Gly Ser Thr Pro Leu Thr Arg Met Pro Val Ser Thr Thr Met
       1040                1045                1050

Val Ala Ser Ser Glu Thr Ser Thr Leu Ser Thr Thr Pro Ala Asp
       1055                1060                1065

Thr Ser Thr Pro Val Thr Thr Tyr Ser Gln Ala Ser Ser Ser Ser
       1070                1075                1080

Thr Thr Ala Asp Gly Thr Ser Met Pro Thr Ser Thr Tyr Ser Glu
       1085                1090                1095

Gly Ser Thr Pro Leu Thr Ser Val Pro Val Ser Thr Arg Leu Val
       1100                1105                1110

Val Ser Ser Glu Ala Ser Thr Leu Ser Thr Thr Pro Val Asp Thr
       1115                1120                1125

Ser Ile Pro Val Thr Thr Ser Thr Glu Ala Ser Ser Pro Thr
       1130                1135                1140

Thr Ala Glu Gly Thr Ser Ile Pro Thr Ser Pro Ser Glu Gly
       1145                1150                1155

Thr Thr Pro Leu Ala Ser Met Pro Val Ser Thr Thr Leu Val Val
       1160                1165                1170

Ser Ser Glu Ala Asn Thr Leu Ser Thr Thr Pro Val Asp Ser Lys
       1175                1180                1185

Thr Gln Val Ala Thr Ser Thr Glu Ala Ser Ser Pro Pro Pro Thr
       1190                1195                1200

Ala Glu Val Thr Ser Met Pro Thr Ser Thr Pro Gly Glu Arg Ser
       1205                1210                1215

Thr Pro Leu Thr Ser Met Pro Val Arg His Thr Pro Val Ala Ser
       1220                1225                1230

Ser Glu Ala Ser Thr Leu Ser Thr Ser Pro Val Asp Thr Ser Thr
       1235                1240                1245

Pro Val Thr Thr Ser Ala Glu Thr Ser Ser Ser Pro Thr Thr Ala
       1250                1255                1260

Glu Gly Thr Ser Leu Pro Ser Thr Thr Ser Glu Gly Ser Thr
       1265                1270                1275

Leu Leu Thr Ser Ile Pro Val Ser Thr Thr Leu Val Thr Ser Pro
       1280                1285                1290

Glu Ala Ser Thr Leu Leu Thr Thr Pro Val Asp Thr Lys Gly Pro
       1295                1300                1305

Val Val Thr Ser Asn Glu Val Ser Ser Ser Pro Thr Pro Ala Glu
       1310                1315                1320

Gly Thr Ser Met Pro Thr Ser Thr Tyr Ser Glu Gly Arg Thr Pro
       1325                1330                1335

Leu Thr Ser Ile Pro Val Asn Thr Thr Leu Val Ala Ser Ser Ala
       1340                1345                1350

Ile Ser Ile Leu Ser Thr Thr Pro Val Asp Asn Ser Thr Pro Val
       1355                1360                1365
```

-continued

```
Thr Thr Ser Thr Glu Ala Cys Ser Ser Pro Thr Ser Glu Gly
    1370            1375            1380

Thr Ser Met Pro Asn Ser Asn Pro Ser Glu Gly Thr Thr Pro Leu
    1385            1390            1395

Thr Ser Ile Pro Val Ser Thr Thr Pro Val Val Ser Ser Glu Ala
    1400            1405            1410

Ser Thr Leu Ser Ala Thr Pro Val Asp Thr Ser Thr Pro Gly Thr
    1415            1420            1425

Thr Ser Ala Glu Ala Thr Ser Ser Pro Thr Thr Ala Glu Gly Ile
    1430            1435            1440

Ser Ile Pro Thr Ser Thr Pro Ser Glu Gly Lys Thr Pro Leu Lys
    1445            1450            1455

Ser Ile Pro Val Ser Asn Thr Pro Val Ala Asn Ser Glu Ala Ser
    1460            1465            1470

Thr Leu Ser Thr Thr Pro Val Asp Ser Asn Ser Pro Val Val Thr
    1475            1480            1485

Ser Thr Ala Val Ser Ser Ser Pro Thr Pro Ala Glu Gly Thr Ser
    1490            1495            1500

Ile Ala Ile Ser Thr Pro Ser Glu Gly Ser Thr Ala Leu Thr Ser
    1505            1510            1515

Ile Pro Val Ser Thr Thr Thr Val Ala Ser Ser Glu Ile Asn Ser
    1520            1525            1530

Leu Ser Thr Thr Pro Ala Val Thr Ser Thr Pro Val Thr Thr Tyr
    1535            1540            1545

Ser Gln Ala Ser Ser Ser Pro Thr Thr Ala Asp Gly Thr Ser Met
    1550            1555            1560

Gln Thr Ser Thr Tyr Ser Glu Gly Ser Thr Pro Leu Thr Ser Leu
    1565            1570            1575

Pro Val Ser Thr Met Leu Val Val Ser Ser Glu Ala Asn Thr Leu
    1580            1585            1590

Ser Thr Thr Pro Ile Asp Ser Lys Thr Gln Val Thr Ala Ser Thr
    1595            1600            1605

Glu Ala Ser Ser Ser Thr Thr Ala Glu Gly Ser Ser Met Thr Ile
    1610            1615            1620

Ser Thr Pro Ser Glu Gly Ser Pro Leu Leu Thr Ser Ile Pro Val
    1625            1630            1635

Ser Thr Thr Pro Val Ala Ser Pro Glu Ala Ser Thr Leu Ser Thr
    1640            1645            1650

Thr Pro Val Asp Ser Asn Ser Pro Val Ile Thr Ser Thr Glu Val
    1655            1660            1665

Ser Ser Ser Pro Thr Pro Ala Glu Gly Thr Ser Met Pro Thr Ser
    1670            1675            1680

Thr Tyr Thr Glu Gly Arg Thr Pro Leu Thr Ser Ile Thr Val Arg
    1685            1690            1695

Thr Thr Pro Val Ala Ser Ala Ile Ser Thr Leu Ser Thr Thr
    1700            1705            1710

Pro Val Asp Asn Ser Thr Pro Val Thr Ser Thr Glu Ala Arg
    1715            1720            1725

Ser Ser Pro Thr Thr Ser Glu Gly Thr Ser Met Pro Asn Ser Thr
    1730            1735            1740

Pro Ser Glu Gly Thr Thr Pro Leu Thr Ser Ile Pro Val Ser Thr
    1745            1750            1755

Thr Pro Val Leu Ser Ser Glu Ala Ser Thr Leu Ser Ala Thr Pro
```

```
                1760                1765                1770

Ile Asp Thr Ser Thr Pro Val Thr Thr Ser Thr Glu Ala Thr Ser
1775                1780                1785

Ser Pro Thr Thr Ala Glu Gly Thr Ser Ile Pro Thr Ser Thr Leu
1790                1795                1800

Ser Glu Gly Met Thr Pro Leu Thr Ser Thr Pro Val Ser His Thr
1805                1810                1815

Leu Val Ala Asn Ser Glu Ala Ser Thr Leu Ser Thr Thr Pro Val
1820                1825                1830

Asp Ser Asn Ser Pro Val Val Thr Ser Thr Ala Val Ser Ser Ser
1835                1840                1845

Pro Thr Pro Ala Glu Gly Thr Ser Ile Ala Thr Ser Thr Pro Ser
1850                1855                1860

Glu Gly Ser Thr Ala Leu Thr Ser Ile Pro Val Ser Thr Thr Thr
1865                1870                1875

Val Ala Ser Ser Glu Thr Asn Thr Leu Ser Thr Thr Pro Ala Val
1880                1885                1890

Thr Ser Thr Pro Val Thr Thr Tyr Ala Gln Val Ser Ser Ser Pro
1895                1900                1905

Thr Thr Ala Asp Gly Ser Ser Met Pro Thr Ser Thr Pro Arg Glu
1910                1915                1920

Gly Arg Pro Pro Leu Thr Ser Ile Pro Val Ser Thr Thr Thr Val
1925                1930                1935

Ala Ser Ser Glu Ile Asn Thr Leu Ser Thr Thr Leu Ala Asp Thr
1940                1945                1950

Arg Thr Pro Val Thr Thr Tyr Ser Gln Ala Ser Ser Ser Pro Thr
1955                1960                1965

Thr Ala Asp Gly Thr Ser Met Pro Thr Pro Ala Tyr Ser Glu Gly
1970                1975                1980

Ser Thr Pro Leu Thr Ser Met Pro Leu Ser Thr Thr Leu Val Val
1985                1990                1995

Ser Ser Glu Ala Ser Thr Leu Ser Thr Thr Pro Val Asp Thr Ser
2000                2005                2010

Thr Pro Ala Thr Thr Ser Thr Glu Gly Ser Ser Ser Pro Thr Thr
2015                2020                2025

Ala Gly Gly Thr Ser Ile Gln Thr Ser Thr Pro Ser Glu Arg Thr
2030                2035                2040

Thr Pro Leu Ala Gly Met Pro Val Ser Thr Thr Leu Val Val Ser
2045                2050                2055

Ser Glu Gly Asn Thr Leu Ser Thr Thr Pro Val Asp Ser Lys Thr
2060                2065                2070

Gln Val Thr Asn Ser Thr Glu Ala Ser Ser Ser Ala Thr Ala Glu
2075                2080                2085

Gly Ser Ser Met Thr Ile Ser Ala Pro Ser Glu Gly Ser Pro Leu
2090                2095                2100

Leu Thr Ser Ile Pro Leu Ser Thr Thr Pro Val Ala Ser Pro Glu
2105                2110                2115

Ala Ser Thr Leu Ser Thr Thr Pro Val Asp Ser Asn Ser Pro Val
2120                2125                2130

Ile Thr Ser Thr Glu Val Ser Ser Ser Pro Ile Pro Thr Glu Gly
2135                2140                2145

Thr Ser Met Gln Thr Ser Thr Tyr Ser Asp Arg Arg Thr Pro Leu
2150                2155                2160
```

```
Thr Ser Met Pro Val Ser Thr Val Val Ala Ser Ser Ala Ile
2165            2170            2175

Ser Thr Leu Ser Thr Thr Pro Val Asp Thr Ser Thr Pro Val Thr
2180            2185            2190

Asn Ser Thr Glu Ala Arg Ser Ser Pro Thr Thr Ser Glu Gly Thr
2195            2200            2205

Ser Met Pro Thr Ser Thr Pro Ser Glu Gly Ser Thr Pro Phe Thr
2210            2215            2220

Ser Met Pro Val Ser Thr Met Pro Val Val Thr Ser Glu Ala Ser
2225            2230            2235

Thr Leu Ser Ala Thr Pro Val Asp Thr Ser Thr Pro Val Thr Thr
2240            2245            2250

Ser Thr Glu Ala Thr Ser Ser Pro Thr Thr Ala Glu Gly Thr Ser
2255            2260            2265

Ile Pro Thr Ser Thr Leu Ser Glu Gly Thr Thr Pro Leu Thr Ser
2270            2275            2280

Ile Pro Val Ser His Thr Leu Val Ala Asn Ser Glu Val Ser Thr
2285            2290            2295

Leu Ser Thr Thr Pro Val Asp Ser Asn Thr Pro Phe Thr Thr Ser
2300            2305            2310

Thr Glu Ala Ser Ser Pro Pro Thr Ala Glu Gly Thr Ser Met
2315            2320            2325

Pro Thr Ser Thr Ser Ser Glu Gly Asn Thr Pro Leu Thr Arg Met
2330            2335            2340

Pro Val Ser Thr Thr Met Val Ala Ser Phe Glu Thr Ser Thr Leu
2345            2350            2355

Ser Thr Thr Pro Ala Asp Thr Ser Thr Pro Val Thr Thr Tyr Ser
2360            2365            2370

Gln Ala Gly Ser Ser Pro Thr Thr Ala Asp Asp Thr Ser Met Pro
2375            2380            2385

Thr Ser Thr Tyr Ser Glu Gly Ser Thr Pro Leu Thr Ser Val Pro
2390            2395            2400

Val Ser Thr Met Pro Val Val Ser Ser Glu Ala Ser Thr His Ser
2405            2410            2415

Thr Thr Pro Val Asp Thr Ser Thr Pro Val Thr Thr Ser Thr Glu
2420            2425            2430

Ala Ser Ser Ser Pro Thr Thr Ala Glu Gly Thr Ser Ile Pro Thr
2435            2440            2445

Ser Pro Pro Ser Glu Gly Thr Thr Pro Leu Ala Ser Met Pro Val
2450            2455            2460

Ser Thr Thr Pro Val Val Ser Ser Glu Ala Gly Thr Leu Ser Thr
2465            2470            2475

Thr Pro Val Asp Thr Ser Thr Pro Met Thr Thr Ser Thr Glu Ala
2480            2485            2490

Ser Ser Ser Pro Thr Thr Ala Glu Asp Ile Val Pro Ile Ser
2495            2500            2505

Thr Ala Ser Glu Gly Ser Thr Leu Leu Thr Ser Ile Pro Val Ser
2510            2515            2520

Thr Thr Pro Val Ala Ser Pro Glu Ala Ser Thr Leu Ser Thr Thr
2525            2530            2535

Pro Val Asp Ser Asn Ser Pro Val Val Thr Ser Thr Glu Ile Ser
2540            2545            2550

Ser Ser Ala Thr Ser Ala Glu Gly Thr Ser Met Pro Thr Ser Thr
2555            2560            2565
```

```
Tyr Ser Glu Gly Ser Thr Pro Leu Arg Ser Met Pro Val Ser Thr
2570                2575                2580
Lys Pro Leu Ala Ser Ser Glu Ala Ser Thr Leu Ser Thr Thr Pro
2585                2590                2595
Val Asp Thr Ser Ile Pro Val Thr Thr Ser Thr Glu Thr Ser Ser
2600                2605                2610
Ser Pro Thr Thr Ala Lys Asp Thr Ser Met Pro Ile Ser Thr Pro
2615                2620                2625
Ser Glu Val Ser Thr Ser Leu Thr Ser Ile Leu Val Ser Thr Met
2630                2635                2640
Pro Val Ala Ser Ser Glu Ala Ser Thr Leu Ser Thr Thr Pro Val
2645                2650                2655
Asp Thr Arg Thr Leu Val Thr Thr Ser Gly Thr Ser Ser Ser
2660                2665                2670
Pro Thr Thr Ala Glu Gly Ser Ser Met Pro Thr Ser Thr Pro Gly
2675                2680                2685
Glu Arg Ser Thr Pro Leu Thr Asn Ile Leu Val Ser Thr Thr Leu
2690                2695                2700
Leu Ala Asn Ser Glu Ala Ser Thr Leu Ser Thr Thr Pro Val Asp
2705                2710                2715
Thr Ser Thr Pro Val Thr Thr Ser Ala Glu Ala Ser Ser Ser Pro
2720                2725                2730
Thr Thr Ala Glu Gly Thr Ser Met Arg Ile Ser Thr Pro Ser Asp
2735                2740                2745
Gly Ser Thr Pro Leu Thr Ser Ile Leu Val Ser Thr Leu Pro Val
2750                2755                2760
Ala Ser Ser Glu Ala Ser Thr Val Ser Thr Thr Ala Val Asp Thr
2765                2770                2775
Ser Ile Pro Val Thr Thr Ser Thr Glu Ala Ser Ser Ser Pro Thr
2780                2785                2790
Thr Ala Glu Val Thr Ser Met Pro Thr Ser Thr Pro Ser Glu Thr
2795                2800                2805
Ser Thr Pro Leu Thr Ser Met Pro Val Asn His Thr Pro Val Ala
2810                2815                2820
Ser Ser Glu Ala Gly Thr Leu Ser Thr Thr Pro Val Asp Thr Ser
2825                2830                2835
Thr Pro Val Thr Thr Ser Lys Ala Ser Ser Ser Pro Thr Thr
2840                2845                2850
Ala Glu Gly Ile Val Val Pro Ile Ser Thr Ala Ser Glu Gly Ser
2855                2860                2865
Thr Leu Leu Thr Ser Ile Pro Val Ser Thr Thr Pro Val Ala Ser
2870                2875                2880
Ser Glu Ala Ser Thr Leu Ser Thr Thr Pro Val Asp Thr Ser Ile
2885                2890                2895
Pro Val Thr Thr Ser Thr Glu Gly Ser Ser Ser Pro Thr Thr Ala
2900                2905                2910
Glu Gly Thr Ser Met Pro Ile Ser Thr Pro Ser Glu Val Ser Thr
2915                2920                2925
Pro Leu Thr Ser Ile Leu Val Ser Thr Val Pro Val Ala Gly Ser
2930                2935                2940
Glu Ala Ser Thr Leu Ser Thr Pro Val Asp Thr Arg Thr Pro
2945                2950                2955
Val Thr Thr Ser Ala Glu Ala Ser Ser Ser Pro Thr Thr Ala Glu
```

-continued

```
                2960                2965                2970

Gly Thr Ser Met Pro Ile Ser Thr Pro Gly Glu Arg Arg Thr Pro
        2975                2980                2985

Leu Thr Ser Met Ser Val Ser Thr Met Pro Val Ala Ser Ser Glu
        2990                2995                3000

Ala Ser Thr Leu Ser Arg Thr Pro Ala Asp Thr Ser Thr Pro Val
        3005                3010                3015

Thr Thr Ser Thr Glu Ala Ser Ser Ser Pro Thr Thr Ala Glu Gly
        3020                3025                3030

Thr Gly Ile Pro Ile Ser Thr Pro Ser Glu Gly Ser Thr Pro Leu
        3035                3040                3045

Thr Ser Ile Pro Val Ser Thr Thr Pro Val Ala Ile Pro Glu Ala
        3050                3055                3060

Ser Thr Leu Ser Thr Thr Pro Val Asp Ser Asn Ser Pro Val Val
        3065                3070                3075

Thr Ser Thr Glu Val Ser Ser Ser Pro Thr Pro Ala Glu Gly Thr
        3080                3085                3090

Ser Met Pro Ile Ser Thr Tyr Ser Glu Gly Ser Thr Pro Leu Thr
        3095                3100                3105

Gly Val Pro Val Ser Thr Thr Pro Val Thr Ser Ser Ala Ile Ser
        3110                3115                3120

Thr Leu Ser Thr Thr Pro Val Asp Thr Ser Thr Pro Val Thr Thr
        3125                3130                3135

Ser Thr Glu Ala His Ser Ser Pro Thr Thr Ser Glu Gly Thr Ser
        3140                3145                3150

Met Pro Thr Ser Thr Pro Ser Glu Gly Ser Thr Pro Leu Thr Tyr
        3155                3160                3165

Met Pro Val Ser Thr Met Leu Val Val Ser Ser Glu Asp Ser Thr
        3170                3175                3180

Leu Ser Ala Thr Pro Val Asp Thr Ser Thr Pro Val Thr Thr Ser
        3185                3190                3195

Thr Glu Ala Thr Ser Ser Thr Ala Glu Gly Thr Ser Ile Pro
        3200                3205                3210

Thr Ser Thr Pro Ser Glu Gly Met Thr Pro Leu Thr Ser Val Pro
        3215                3220                3225

Val Ser Asn Thr Pro Val Ala Ser Ser Glu Ala Ser Ile Leu Ser
        3230                3235                3240

Thr Thr Pro Val Asp Ser Asn Thr Pro Leu Thr Thr Ser Thr Glu
        3245                3250                3255

Ala Ser Ser Ser Pro Pro Thr Ala Glu Gly Thr Ser Met Pro Thr
        3260                3265                3270

Ser Thr Pro Ser Glu Gly Ser Thr Pro Leu Thr Ser Met Pro Val
        3275                3280                3285

Ser Thr Thr Thr Val Ala Ser Ser Glu Thr Ser Thr Leu Ser Thr
        3290                3295                3300

Thr Pro Ala Asp Thr Ser Thr Pro Val Thr Thr Tyr Ser Gln Ala
        3305                3310                3315

Ser Ser Ser Pro Pro Ile Ala Asp Gly Thr Ser Met Pro Thr Ser
        3320                3325                3330

Thr Tyr Ser Glu Gly Ser Thr Pro Leu Thr Asn Met Ser Phe Ser
        3335                3340                3345

Thr Thr Pro Val Val Ser Ser Glu Ala Ser Thr Leu Ser Thr Thr
        3350                3355                3360
```

-continued

| | | | | | | | | | | | |
|---|---|---|---|---|---|---|---|---|---|---|---|
|Pro|Val|Asp|Thr|Ser|Thr|Pro|Val|Thr|Ser|Thr|Glu Ala Ser|
|3365| | | | |3370| | | |3375| | |

Leu Ser Pro Thr Thr Ala Glu Gly Thr Ser Ile Pro Thr Ser Ser
3380            3385            3390

Pro Ser Glu Gly Thr Thr Pro Leu Ala Ser Met Pro Val Ser Thr
3395            3400            3405

Thr Pro Val Val Ser Ser Glu Val Asn Thr Leu Ser Thr Thr Pro
3410            3415            3420

Val Asp Ser Asn Thr Leu Val Thr Thr Ser Thr Glu Ala Ser Ser
3425            3430            3435

Ser Pro Thr Ile Ala Glu Gly Thr Ser Leu Pro Thr Ser Thr Thr
3440            3445            3450

Ser Glu Gly Ser Thr Pro Leu Ser Ile Met Pro Leu Ser Thr Thr
3455            3460            3465

Pro Val Ala Ser Ser Glu Ala Ser Thr Leu Ser Thr Thr Pro Val
3470            3475            3480

Asp Thr Ser Thr Pro Val Thr Thr Ser Ser Pro Thr Asn Ser Ser
3485            3490            3495

Pro Thr Thr Ala Glu Val Thr Ser Met Pro Thr Ser Thr Ala Gly
3500            3505            3510

Glu Gly Ser Thr Pro Leu Thr Asn Met Pro Val Ser Thr Thr Pro
3515            3520            3525

Val Ala Ser Ser Glu Ala Ser Thr Leu Ser Thr Thr Pro Val Asp
3530            3535            3540

Ser Asn Thr Phe Val Thr Ser Ser Ser Gln Ala Ser Ser Ser Pro
3545            3550            3555

Ala Thr Leu Gln Val Thr Thr Met Arg Met Ser Thr Pro Ser Glu
3560            3565            3570

Gly Ser Ser Ser Leu Thr Thr Met Leu Leu Ser Ser Thr Tyr Val
3575            3580            3585

Thr Ser Ser Glu Ala Ser Thr Pro Ser Thr Pro Ser Val Asp Arg
3590            3595            3600

Ser Thr Pro Val Thr Thr Ser Thr Gln Ser Asn Ser Thr Pro Thr
3605            3610            3615

Pro Pro Glu Val Ile Thr Leu Pro Met Ser Thr Pro Ser Glu Val
3620            3625            3630

Ser Thr Pro Leu Thr Ile Met Pro Val Ser Thr Thr Ser Val Thr
3635            3640            3645

Ile Ser Glu Ala Gly Thr Ala Ser Thr Leu Pro Val Asp Thr Ser
3650            3655            3660

Thr Pro Val Ile Thr Ser Thr Gln Val Ser Ser Ser Pro Val Thr
3665            3670            3675

Pro Glu Gly Thr Thr Met Pro Ile Trp Thr Pro Ser Glu Gly Ser
3680            3685            3690

Thr Pro Leu Thr Thr Met Pro Val Ser Thr Thr Arg Val Thr Ser
3695            3700            3705

Ser Glu Gly Ser Thr Leu Ser Thr Pro Ser Val Val Thr Ser Thr
3710            3715            3720

Pro Val Thr Thr Ser Thr Glu Ala Ile Ser Ser Ser Ala Thr Leu
3725            3730            3735

Asp Ser Thr Thr Met Ser Val Ser Met Pro Met Glu Ile Ser Thr
3740            3745            3750

Leu Gly Thr Thr Ile Leu Val Ser Thr Thr Pro Val Thr Arg Phe
3755            3760            3765

```
Pro Glu Ser Ser Thr Pro Ser Ile Pro Ser Val Tyr Thr Ser Met
    3770            3775            3780

Ser Met Thr Thr Ala Ser Glu Gly Ser Ser Pro Thr Thr Leu
    3785            3790            3795

Glu Gly Thr Thr Thr Met Pro Met Ser Thr Ser Glu Arg Ser
    3800            3805            3810

Thr Leu Leu Thr Thr Val Leu Ile Ser Pro Ile Ser Val Met Ser
    3815            3820            3825

Pro Ser Glu Ala Ser Thr Leu Ser Thr Pro Pro Gly Asp Thr Ser
    3830            3835            3840

Thr Pro Leu Leu Thr Ser Thr Lys Ala Gly Ser Phe Ser Ile Pro
    3845            3850            3855

Ala Glu Val Thr Thr Ile Arg Ile Ser Ile Thr Ser Glu Arg Ser
    3860            3865            3870

Thr Pro Leu Thr Thr Leu Leu Val Ser Thr Thr Leu Pro Thr Ser
    3875            3880            3885

Phe Pro Gly Ala Ser Ile Ala Ser Thr Pro Pro Leu Asp Thr Ser
    3890            3895            3900

Thr Thr Phe Thr Pro Ser Thr Asp Thr Ala Ser Thr Pro Thr Ile
    3905            3910            3915

Pro Val Ala Thr Thr Ile Ser Val Ser Val Ile Thr Glu Gly Ser
    3920            3925            3930

Thr Pro Gly Thr Thr Ile Phe Ile Pro Ser Thr Pro Val Thr Ser
    3935            3940            3945

Ser Thr Ala Asp Val Phe Pro Ala Thr Thr Gly Ala Val Ser Thr
    3950            3955            3960

Pro Val Ile Thr Ser Thr Glu Leu Asn Thr Pro Ser Thr Ser Ser
    3965            3970            3975

Ser Ser Thr Thr Thr Ser Phe Ser Thr Thr Lys Glu Phe Thr Thr
    3980            3985            3990

Pro Ala Met Thr Thr Ala Ala Pro Leu Thr Tyr Val Thr Met Ser
    3995            4000            4005

Thr Ala Pro Ser Thr Pro Arg Thr Thr Ser Arg Gly Cys Thr Thr
    4010            4015            4020

Ser Ala Ser Thr Leu Ser Ala Thr Ser Thr Pro His Thr Ser Thr
    4025            4030            4035

Ser Val Thr Thr Arg Pro Val Thr Pro Ser Ser Glu Ser Ser Arg
    4040            4045            4050

Pro Ser Thr Ile Thr Ser His Thr Ile Pro Pro Thr Phe Pro Pro
    4055            4060            4065

Ala His Ser Ser Thr Pro Pro Thr Thr Ser Ala Ser Ser Thr Thr
    4070            4075            4080

Val Asn Pro Glu Ala Val Thr Thr Met Thr Thr Arg Thr Lys Pro
    4085            4090            4095

Ser Thr Arg Thr Thr Ser Phe Pro Thr Val Thr Thr Thr Ala Val
    4100            4105            4110

Pro Thr Asn Thr Thr Ile Lys Ser Asn Pro Thr Ser Thr Pro Thr
    4115            4120            4125

Val Pro Arg Thr Thr Thr Cys Phe Gly Asp Gly Cys Gln Asn Thr
    4130            4135            4140

Ala Ser Arg Cys Lys Asn Gly Gly Thr Trp Asp Gly Leu Lys Cys
    4145            4150            4155

Gln Cys Pro Asn Leu Tyr Tyr Gly Glu Leu Cys Glu Glu Val Val
```

```
              4160           4165               4170

Ser  Ser  Ile  Asp  Ile  Gly  Pro  Pro  Glu  Thr  Ile  Ser  Ala  Gln  Met
     4175                4180                4185

Glu  Leu  Thr  Val  Thr  Val  Thr  Ser  Val  Lys  Phe  Thr  Glu  Glu  Leu
     4190                4195                4200

Lys  Asn  His  Ser  Ser  Gln  Glu  Phe  Gln  Glu  Phe  Lys  Gln  Thr  Phe
     4205                4210                4215

Thr  Glu  Gln  Met  Asn  Ile  Val  Tyr  Ser  Gly  Ile  Pro  Glu  Tyr  Val
     4220                4225                4230

Gly  Val  Asn  Ile  Thr  Lys  Leu  Arg  Leu  Gly  Ser  Val  Val  Val  Glu
     4235                4240                4245

His  Asp  Val  Leu  Leu  Arg  Thr  Lys  Tyr  Thr  Pro  Glu  Tyr  Lys  Thr
     4250                4255                4260

Val  Leu  Asp  Asn  Ala  Thr  Glu  Val  Val  Lys  Glu  Lys  Ile  Thr  Lys
     4265                4270                4275

Val  Thr  Thr  Gln  Gln  Ile  Met  Ile  Asn  Asp  Ile  Cys  Ser  Asp  Met
     4280                4285                4290

Met  Cys  Phe  Asn  Thr  Thr  Gly  Thr  Gln  Val  Gln  Asn  Ile  Thr  Val
     4295                4300                4305

Thr  Gln  Tyr  Asp  Pro  Glu  Glu  Asp  Cys  Arg  Lys  Met  Ala  Lys  Glu
     4310                4315                4320

Tyr  Gly  Asp  Tyr  Phe  Val  Val  Glu  Tyr  Arg  Asp  Gln  Lys  Pro  Tyr
     4325                4330                4335

Cys  Ile  Ser  Pro  Cys  Glu  Pro  Gly  Phe  Ser  Val  Ser  Lys  Asn  Cys
     4340                4345                4350

Asn  Leu  Gly  Lys  Cys  Gln  Met  Ser  Leu  Ser  Gly  Pro  Gln  Cys  Leu
     4355                4360                4365

Cys  Val  Thr  Thr  Glu  Thr  His  Trp  Tyr  Ser  Gly  Glu  Thr  Cys  Asn
     4370                4375                4380

Gln  Gly  Thr  Gln  Lys  Ser  Leu  Val  Tyr  Gly  Leu  Val  Gly  Ala  Gly
     4385                4390                4395

Val  Val  Leu  Met  Leu  Ile  Ile  Leu  Val  Ala  Leu  Leu  Met  Leu  Val
     4400                4405                4410

Phe  Arg  Ser  Lys  Arg  Glu  Val  Lys  Arg  Gln  Lys  Tyr  Arg  Leu  Ser
     4415                4420                4425

Gln  Leu  Tyr  Lys  Trp  Gln  Glu  Glu  Asp  Ser  Gly  Pro  Ala  Pro  Gly
     4430                4435                4440

Thr  Phe  Gln  Asn  Ile  Gly  Phe  Asp  Ile  Cys  Gln  Asp  Asp  Asp  Ser
     4445                4450                4455

Ile  His  Leu  Glu  Ser  Ile  Tyr  Ser  Asn  Phe  Gln  Pro  Ser  Leu  Arg
     4460                4465                4470

His  Ile  Asp  Pro  Glu  Thr  Lys  Ile  Arg  Ile  Gln  Arg  Pro  Gln  Val
     4475                4480                4485

Met  Thr  Thr  Ser  Phe
     4490

<210> SEQ ID NO 3
<211> LENGTH: 215
<212> TYPE: PRT
<213> ORGANISM: homo sapiens

<400> SEQUENCE: 3

Ile  Asp  Ile  Gly  Pro  Pro  Glu  Thr  Ile  Ser  Ala  Gln  Met  Glu  Leu  Thr
1                 5                    10                   15

Val  Thr  Val  Thr  Ser  Val  Lys  Phe  Thr  Glu  Glu  Leu  Lys  Asn  His  Ser
```

```
                    20                  25                  30
Ser Gln Glu Phe Gln Glu Phe Lys Gln Thr Phe Thr Glu Gln Met Asn
                35                  40                  45
Ile Val Tyr Ser Gly Ile Pro Glu Tyr Val Gly Val Asn Ile Thr Lys
            50                  55                  60
Leu Arg Leu Gly Ser Val Val Glu His Asp Val Leu Leu Arg Thr
65                  70                  75                  80
Lys Tyr Thr Pro Glu Tyr Lys Thr Val Leu Asp Asn Ala Thr Glu Val
                85                  90                  95
Val Lys Glu Lys Ile Thr Lys Val Thr Thr Gln Gln Ile Met Ile Asn
            100                 105                 110
Asp Ile Cys Ser Asp Met Met Cys Phe Asn Thr Thr Gly Thr Gln Val
        115                 120                 125
Gln Asn Ile Thr Val Thr Gln Tyr Asp Pro Glu Glu Asp Cys Arg Lys
    130                 135                 140
Met Ala Lys Glu Tyr Gly Asp Tyr Phe Val Val Glu Tyr Arg Asp Gln
145                 150                 155                 160
Lys Pro Tyr Cys Ile Ser Pro Cys Glu Pro Gly Phe Ser Val Ser Lys
                165                 170                 175
Asn Cys Asn Leu Gly Lys Cys Gln Met Ser Leu Ser Gly Pro Gln Cys
            180                 185                 190
Leu Cys Val Thr Thr Glu Thr His Trp Tyr Ser Gly Glu Thr Cys Asn
        195                 200                 205
Gln Gly Thr Gln Lys Ser Leu
    210                 215

<210> SEQ ID NO 4
<211> LENGTH: 147
<212> TYPE: PRT
<213> ORGANISM: homo sapiens

<400> SEQUENCE: 4

Ser Val Val Glu His Asp Val Leu Leu Arg Thr Lys Tyr Thr Pro
1               5                   10                  15
Glu Tyr Lys Thr Val Leu Asp Asn Ala Thr Glu Val Val Lys Glu Lys
                20                  25                  30
Ile Thr Lys Val Thr Thr Gln Gln Ile Met Ile Asn Asp Ile Cys Ser
            35                  40                  45
Asp Met Met Cys Phe Asn Thr Thr Gly Thr Gln Val Gln Asn Ile Thr
50                  55                  60
Val Thr Gln Tyr Asp Pro Glu Glu Asp Cys Arg Lys Met Ala Lys Glu
65                  70                  75                  80
Tyr Gly Asp Tyr Phe Val Val Glu Tyr Arg Asp Gln Lys Pro Tyr Cys
                85                  90                  95
Ile Ser Pro Cys Glu Pro Gly Phe Ser Val Ser Lys Asn Cys Asn Leu
            100                 105                 110
Gly Lys Cys Gln Met Ser Leu Ser Gly Pro Gln Cys Leu Cys Val Thr
        115                 120                 125
Thr Glu Thr His Trp Tyr Ser Gly Glu Thr Cys Asn Gln Gly Thr Gln
    130                 135                 140
Lys Ser Leu
145

<210> SEQ ID NO 5
<211> LENGTH: 129
<212> TYPE: PRT
```

<213> ORGANISM: homo sapiens

<400> SEQUENCE: 5

Thr Asn Thr Thr Ile Lys Ser Asn Pro Thr Ser Pro Thr Val Pro
1               5                   10                  15

Arg Thr Thr Thr Cys Phe Gly Asp Gly Cys Gln Asn Thr Ala Ser Arg
            20                  25                  30

Cys Lys Asn Gly Gly Thr Trp Asp Gly Leu Lys Cys Gln Cys Pro Asn
        35                  40                  45

Leu Tyr Tyr Gly Glu Leu Cys Glu Glu Val Val Ser Ser Ile Asp Ile
    50                  55                  60

Gly Pro Pro Glu Thr Ile Ser Ala Gln Met Glu Leu Thr Val Thr Val
65                  70                  75                  80

Thr Ser Val Lys Phe Thr Glu Glu Leu Lys Asn His Ser Ser Gln Glu
                85                  90                  95

Phe Gln Glu Phe Lys Gln Thr Phe Thr Glu Gln Met Asn Ile Val Tyr
            100                 105                 110

Ser Gly Ile Pro Glu Tyr Val Gly Val Asn Ile Thr Lys Leu Arg Leu
        115                 120                 125

Gly

<210> SEQ ID NO 6
<211> LENGTH: 5
<212> TYPE: PRT
<213> ORGANISM: Mus musculus

<400> SEQUENCE: 6

Ser His Trp Met Asn
1               5

<210> SEQ ID NO 7
<211> LENGTH: 17
<212> TYPE: PRT
<213> ORGANISM: Mus musculus

<400> SEQUENCE: 7

Gln Ile Tyr Pro Gly Asp Gly Asp Ile Asn Tyr Asn Gly Lys Phe Lys
1               5                   10                  15

Gly

<210> SEQ ID NO 8
<211> LENGTH: 8
<212> TYPE: PRT
<213> ORGANISM: Mus musculus

<400> SEQUENCE: 8

His Tyr Asn Tyr Ala Met Asp Tyr
1               5

<210> SEQ ID NO 9
<211> LENGTH: 10
<212> TYPE: PRT
<213> ORGANISM: Mus musculus

<400> SEQUENCE: 9

Ser Ala Ser Ser Ser Val Ser Tyr Met Cys
1               5                   10

<210> SEQ ID NO 10
<211> LENGTH: 7
<212> TYPE: PRT

<213> ORGANISM: Mus musculus

<400> SEQUENCE: 10

Arg Thr Ser Asn Leu Ala Ser
1               5

<210> SEQ ID NO 11
<211> LENGTH: 9
<212> TYPE: PRT
<213> ORGANISM: Mus musculus

<400> SEQUENCE: 11

Gln Gln Phe His Ser Tyr Pro Arg Thr
1               5

<210> SEQ ID NO 12
<211> LENGTH: 5
<212> TYPE: PRT
<213> ORGANISM: Mus musculus

<400> SEQUENCE: 12

Thr Tyr Trp Met Asn
1               5

<210> SEQ ID NO 13
<211> LENGTH: 17
<212> TYPE: PRT
<213> ORGANISM: Mus musculus

<400> SEQUENCE: 13

Arg Ile Asp Pro Tyr Asp Ser Glu Thr His Tyr Asn Gln Lys Phe Lys
1               5                   10                  15

Asp

<210> SEQ ID NO 14
<211> LENGTH: 12
<212> TYPE: PRT
<213> ORGANISM: Mus musculus

<400> SEQUENCE: 14

Gly Pro Tyr Tyr Gly Thr Asn Pro Trp Phe Pro Tyr
1               5                   10

<210> SEQ ID NO 15
<211> LENGTH: 11
<212> TYPE: PRT
<213> ORGANISM: Mus musculus

<400> SEQUENCE: 15

Arg Ala Ser Lys Ser Ile Ser Lys Tyr Leu Ala
1               5                   10

<210> SEQ ID NO 16
<211> LENGTH: 7
<212> TYPE: PRT
<213> ORGANISM: Mus musculus

<400> SEQUENCE: 16

Ser Gly Ser Thr Leu Gln Ser
1               5

<210> SEQ ID NO 17
<211> LENGTH: 9
<212> TYPE: PRT
<213> ORGANISM: Mus musculus

<400> SEQUENCE: 17

Gln Gln His His Glu Tyr Pro Tyr Thr
1               5

<210> SEQ ID NO 18
<211> LENGTH: 351
<212> TYPE: DNA
<213> ORGANISM: Mus musculus

<400> SEQUENCE: 18
caggttcagc tgcagcagtc tggggctgag ctggtgaggc ctgggtcctc agcgaagatt      60
tcctgtaagg cttctggcta tgaattcagt agccactgga tgaactgggt gaagcagagg     120
cctggacagg gtcttgagtg gattggacag atctatcctg agatggtga tattaactac      180 aatggaaagt tcaagggtaa agccacactg actgcagaca atcctccag tacagtctac      240 atgcagctca gcagcctaac atctgaggac tctgcggtct atttctgtgc aagacattat     300
aactatgcta tggactactg gggtcaagga acctcagtca ccgtctcctc a              351

<210> SEQ ID NO 19
<211> LENGTH: 117
<212> TYPE: PRT
<213> ORGANISM: Mus musculus

<400> SEQUENCE: 19

Gln Val Gln Leu Gln Gln Ser Gly Ala Glu Leu Val Arg Pro Gly Ser
1               5                   10                  15

Ser Ala Lys Ile Ser Cys Lys Ala Ser Gly Tyr Glu Phe Ser Ser His
            20                  25                  30

Trp Met Asn Trp Val Lys Gln Arg Pro Gly Gln Gly Leu Glu Trp Ile
        35                  40                  45

Gly Gln Ile Tyr Pro Gly Asp Gly Asp Ile Asn Tyr Asn Gly Lys Phe
    50                  55                  60

Lys Gly Lys Ala Thr Leu Thr Ala Asp Lys Ser Ser Ser Thr Val Tyr
65                  70                  75                  80

Met Gln Leu Ser Ser Leu Thr Ser Glu Asp Ser Ala Val Tyr Phe Cys
                85                  90                  95

Ala Arg His Tyr Asn Tyr Ala Met Asp Tyr Trp Gly Gln Gly Thr Ser
            100                 105                 110

Val Thr Val Ser Ser
        115

<210> SEQ ID NO 20
<211> LENGTH: 318
<212> TYPE: DNA
<213> ORGANISM: Mus musculus

<400> SEQUENCE: 20
caaattgttc tcacccagtc tccagcaatc atgtctgcat ctccagggga gaaggtcacc      60
atatcctgca gtgccagctc aagtgtaagt tacatgtgct ggtatcagca gaagccagga     120
tcctctccca aaccctggat ttatcgcaca tccaacctgg cttctggagt ccctgctcgc     180
ttcagtggca gtgggtctgg gacctcttac tctctcacaa tcagcagcat ggaggctgaa     240
gatgctgcca cttattactg ccagcagttt catagttacc cacggacgtt cggtggaggc     300
accaagctgg aaatcaaa                                                   318

<210> SEQ ID NO 21

```
<211> LENGTH: 106
<212> TYPE: PRT
<213> ORGANISM: Mus musculus

<400> SEQUENCE: 21

Gln Ile Val Leu Thr Gln Ser Pro Ala Ile Met Ser Ala Ser Pro Gly
1               5                   10                  15

Glu Lys Val Thr Ile Ser Cys Ser Ala Ser Ser Val Ser Tyr Met
            20                  25                  30

Cys Trp Tyr Gln Gln Lys Pro Gly Ser Ser Pro Lys Pro Trp Ile Tyr
        35                  40                  45

Arg Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Phe His Ser Tyr Pro Arg Thr
                85                  90                  95

Phe Gly Gly Gly Thr Lys Leu Glu Ile Lys
            100                 105

<210> SEQ ID NO 22
<211> LENGTH: 363
<212> TYPE: DNA
<213> ORGANISM: Mus musculus

<400> SEQUENCE: 22
caggtccaac tgcagcagcc tggggctgag ctggtgaggc ctggggcttc agtgaagttg     60
tcctgcaagg cttctggcta cacgttcacc acctactgga tgaactgggt taagcagagg    120
cctgagcaag gccttgagtg gattggaagg attgatcctt acgatagtga aactcactac    180
aatcaaaagt tcaaggacaa ggccatattg actgtagaca atcctccag cacagcctac     240 atgcaactca gcagcctgac atctgaggac tctgcggtct attactgtgc aaggggacct    300
tactacggta ctaaccccetg gtttccttac tggggccaag ggactctggt cactgtctct    360
tca                                                                  363

<210> SEQ ID NO 23
<211> LENGTH: 121
<212> TYPE: PRT
<213> ORGANISM: Mus musculus

<400> SEQUENCE: 23

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Thr Tyr
            20                  25                  30

Trp Met Asn Trp Val Lys Gln Arg Pro Glu Gln Gly Leu Glu Trp Ile
        35                  40                  45

Gly Arg Ile Asp Pro Tyr Asp Ser Glu Thr His Tyr Asn Gln Lys Phe
    50                  55                  60

Lys Asp Lys Ala Ile Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Pro Tyr Tyr Gly Thr Asn Pro Trp Phe Pro Tyr Trp Gly
            100                 105                 110

Gln Gly Thr Leu Val Thr Val Ser Ser
        115                 120
```

<210> SEQ ID NO 24
<211> LENGTH: 321
<212> TYPE: DNA
<213> ORGANISM: Mus musculus

<400> SEQUENCE: 24

```
gatgtccaga taacccagtc tccatcttat cttgctgcat ctcctggaga aaccattact    60
attaattgca gggcaagtaa gagcattagc aaatatttag cctggtatca agagaaacct   120
gggaaaacta ataagcttct tatctactct ggatccactt tgcaatctgg aattccatca   180
aggttcagtg gcagtggatc tggtacagat ttcactctca ccatcagtag cctggagcct   240
gaagattttg caatgtatta ctgtcaacag catcatgaat acccgtacac gttcggaggg   300
gggaccaagc tggaaataaa a                                              321
```

<210> SEQ ID NO 25
<211> LENGTH: 107
<212> TYPE: PRT
<213> ORGANISM: Mus musculus

<400> SEQUENCE: 25

Asp Val Gln Ile Thr Gln Ser Pro Ser Tyr Leu Ala Ala Ser Pro Gly
1               5                   10                  15
Glu Thr Ile Thr Ile Asn Cys Arg Ala Ser Lys Ser Ile Ser Lys Tyr
            20                  25                  30
Leu Ala Trp Tyr Gln Glu Lys Pro Gly Lys Thr Asn Lys Leu Leu Ile
        35                  40                  45
Tyr Ser Gly Ser Thr Leu Gln Ser Gly Ile Pro Ser Arg Phe Ser Gly
    50                  55                  60
Ser Gly Ser Gly Thr Asp Phe Thr Leu Thr Ile Ser Ser Leu Glu Pro
65                  70                  75                  80
Glu Asp Phe Ala Met Tyr Tyr Cys Gln Gln His His Glu Tyr Pro Tyr
                85                  90                  95
Thr Phe Gly Gly Gly Thr Lys Leu Glu Ile Lys
            100                 105

<210> SEQ ID NO 26
<211> LENGTH: 1413
<212> TYPE: DNA
<213> ORGANISM: Artificial
<220> FEATURE:
<223> OTHER INFORMATION: chimeric antibody

<400> SEQUENCE: 26

```
atgggatgga gctatatcat cctcttcttg ttagcaacag ctacatgtgt ccactcccag    60
gtccaactgc agcagcctgg ggctgagctg gtgaggcctg ggcttcagt gaagttgtcc    120
tgcaaggctt ctggctacac gttcaccacc tactggatga actgggttaa gcagaggcct   180
gagcaaggcc ttgagtggat tggaaggatt gatccttacg atagtgaaac tcactacaat   240
caaaagttca ggacaaggc catattgact gtagacaaat cctccagcac agcctacatg   300
caactcagca gcctgacatc tgaggactct gcggtctatt actgtgcaag ggaccttac   360
tacggtacta accctggtt tccttactgg ggccaaggga ctctggtcac tgtctcttca   420
gctagcacca agggcccatc ggtcttcccc ctggcaccct cctccaagag cacctctggg   480
ggcacagcgg ccctgggctg cctggtcaag gactacttcc ccgaaccggt gacggtgtcg   540
tggaactcag gcgccctgac cagcggcgtg cacaccttcc cggctgtcct acagtcctca   600
```

```
ggactctact ccctcagcag cgtggtgacc gtgccctcca gcagcttggg cacccagacc    660
tacatctgca acgtgaatca caagcccagc aacaccaagg tggacaagaa agttgagccc    720
aaatcttgtg acaaaactca cacatgccca ccgtgcccag cacctgaact cctgggggga    780
ccgtcagtct tcctcttccc cccaaaaccc aaggacaccc tcatgatctc ccggacccct    840
gaggtcacat gcgtggtggt ggacgtgagc cacgaagacc ctgaggtcaa gttcaactgg    900
tacgtggacg gcgtggaggt gcataatgcc aagacaaagc cgcgggagga gcagtacaac    960
agcacgtacc gtgtggtcag cgtcctcacc gtcctgcacc aggactggct gaatggcaag   1020
gagtacaagt gcaaggtctc caacaaagcc ctcccagccc ccatcgagaa aaccatctcc   1080
aaagccaaag ggcagccccg agaaccacag gtgtacaccc tgcccccatc ccgggatgag   1140
ctgaccaaga accaggtcag cctgacctgc ctggtcaaag gcttctatcc cagcgacatc   1200
gccgtggagt gggagagcaa tgggcagccg gagaacaact acaagaccac gcctcccgtg   1260
ctggactccg acggctcctt cttcctctac agcaagctca ccgtggacaa gagcaggtgg   1320
cagcagggga acgtcttctc atgctccgtg atgcatgagg ctctgcacaa ccactacacg   1380
cagaagagcc tctccctgtc tccgggtaaa tga                                1413
```

```
<210> SEQ ID NO 27
<211> LENGTH: 470
<212> TYPE: PRT
<213> ORGANISM: Artificial
<220> FEATURE:
<223> OTHER INFORMATION: chimeric antibody

<400> SEQUENCE: 27

Met Gly Trp Ser Tyr Ile Ile Leu Phe Leu Leu Ala Thr Ala Thr Cys
1               5                   10                  15

Val His Ser Gln Val Gln Leu Gln Gln Pro Gly Ala Glu Leu Val Arg
            20                  25                  30

Pro Gly Ala Ser Val Lys Leu Ser Cys Lys Ala Ser Gly Tyr Thr Phe
        35                  40                  45

Thr Thr Tyr Trp Met Asn Trp Val Lys Gln Arg Pro Glu Gln Gly Leu
    50                  55                  60

Glu Trp Ile Gly Arg Ile Asp Pro Tyr Asp Ser Glu Thr His Tyr Asn
65                  70                  75                  80

Gln Lys Phe Lys Asp Lys Ala Ile Leu Thr Val Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Gly Pro Tyr Tyr Gly Thr Asn Pro Trp Phe Pro
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220
```

Val Asn His Lys Pro Ser Asn Thr Lys Val Asp Lys Val Glu Pro
225                 230                 235                 240

Lys Ser Cys Asp Lys Thr His Thr Cys Pro Pro Cys Pro Ala Pro Glu
            245                 250                 255

Leu Leu Gly Gly Pro Ser Val Phe Leu Phe Pro Pro Lys Pro Lys Asp
        260                 265                 270

Thr Leu Met Ile Ser Arg Thr Pro Glu Val Thr Cys Val Val Val Asp
    275                 280                 285

Val Ser His Glu Asp Pro Glu Val Lys Phe Asn Trp Tyr Val Asp Gly
290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
            325                 330                 335

Leu Asn Gly Lys Glu Tyr Lys Cys Lys Val Ser Asn Lys Ala Leu Pro
        340                 345                 350

Ala Pro Ile Glu Lys Thr Ile Ser Lys Ala Lys Gly Gln Pro Arg Glu
    355                 360                 365

Pro Gln Val Tyr Thr Leu Pro Pro Ser Arg Asp Glu Leu Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
            405                 410                 415

Thr Pro Pro Val Leu Asp Ser Asp Gly Ser Phe Phe Leu Tyr Ser Lys
        420                 425                 430

Leu Thr Val Asp Lys Ser Arg Trp Gln Gln Gly Asn Val Phe Ser Cys
    435                 440                 445

Ser Val Met His Glu Ala Leu His Asn His Tyr Thr Gln Lys Ser Leu
450                 455                 460

Ser Leu Ser Pro Gly Lys
465             470

<210> SEQ ID NO 28
<211> LENGTH: 705
<212> TYPE: DNA
<213> ORGANISM: Artificial
<220> FEATURE:
<223> OTHER INFORMATION: chimeric antibody

<400> SEQUENCE: 28
atgaggttcc aggttcaggt tctggggctc cttctgctct ggatatcagg tgcccagtgt    60
gatgtccaga taacccagtc tccatcttat cttgctgcat ctcctggaga aaccattact   120
attaattgca gggcaagtaa gagcattagc aaatatttag cctggtatca agagaaacct   180
gggaaaacta taagcttcta tctactctgg atccacttt gcaatctgg aattccatca    240 aggttcagtg gcagtggatc tggtacagat ttcactctca ccatcagtag cctggagcct   300
gaagattttg caatgtatta ctgtcaacag catcatgaat acccgtacac gttcggaggg   360
gggaccaagc tggaaataaa acgtacggtg gctgcaccat ctgtcttcat cttcccgcca   420
tctgatgagc agttgaaatc tggaactgcc tctgttgtgt gcctgctgaa taacttctat   480
cccagagagg ccaaagtaca gtggaaggtg gataacgccc tccaatcggg taactcccag   540
gagagtgtca cagagcagga cagcaaggac agcacctaca gcctcagcag caccctgacg   600
ctgagcaaag cagactacga gaaacacaaa gtctacgcct gcgaagtcac ccatcagggc   660

```
ctgagctcgc cgtcacaaa gagcttcaac aggggagagt gttga                             705
```

<210> SEQ ID NO 29
<211> LENGTH: 234
<212> TYPE: PRT
<213> ORGANISM: Artificial
<220> FEATURE:
<223> OTHER INFORMATION: chimeric antibody

<400> SEQUENCE: 29

```
Met Arg Phe Gln Val Gln Val Leu Gly Leu Leu Leu Trp Ile Ser
1               5                   10                  15

Gly Ala Gln Cys Asp Val Gln Ile Thr Gln Ser Pro Ser Tyr Leu Ala
            20                  25                  30

Ala Ser Pro Gly Glu Thr Ile Thr Ile Asn Cys Arg Ala Ser Lys Ser
        35                  40                  45

Ile Ser Lys Tyr Leu Ala Trp Tyr Gln Glu Lys Pro Gly Lys Thr Asn
    50                  55                  60

Lys Leu Leu Ile Tyr Ser Gly Ser Thr Leu Gln Ser Gly Ile Pro Ser
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Met Tyr Tyr Cys Gln Gln His His
            100                 105                 110

Glu Tyr Pro Tyr Thr Phe Gly Gly Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 30
<211> LENGTH: 27
<212> TYPE: DNA
<213> ORGANISM: homo sapiens

<400> SEQUENCE: 30

```
tccaacaacc tctgcctcct ccacgac                                                27
```

<210> SEQ ID NO 31
<211> LENGTH: 27
<212> TYPE: DNA
<213> ORGANISM: homo sapiens

<400> SEQUENCE: 31

```
tccattcttg cagcgagagg ccgtatt                                                27
```

<210> SEQ ID NO 32
<211> LENGTH: 91

```
<212> TYPE: DNA
<213> ORGANISM: Artificial
<220> FEATURE:
<223> OTHER INFORMATION: PCR primer

<400> SEQUENCE: 32
taagaattcc accatggact ggacctggag gttcctcttt gtggtggcag cagctacagg    60
tgtccagtcc acgaatacta caattaagag c                                  91

<210> SEQ ID NO 33
<211> LENGTH: 41
<212> TYPE: DNA
<213> ORGANISM: Artificial
<220> FEATURE:
<223> OTHER INFORMATION: PCR primer

<400> SEQUENCE: 33
ttgtcggtcc gcgaggttcc agactcttct gggtgccctg g                       41

<210> SEQ ID NO 34
<211> LENGTH: 1587
<212> TYPE: DNA
<213> ORGANISM: Artificial
<220> FEATURE:
<223> OTHER INFORMATION: Muc17 fusion protein

<400> SEQUENCE: 34
atggactgga cctggaggtt cctctttgtg gtggcagcag ctacaggtgt ccagtccacg    60
aatactacaa ttaagagcaa ccccaccctca actcctactg tgccaagaac acaacatgc   120 tttggagatg ggtgccagaa tacggcctct cgctgcaaga atggaggcac ctgggatggg   180
ctcaagtgcc agtgtcccaa cctctattat ggggagttgt gtgaggaggt ggtcagcagc   240
attgacatag gccaccggga gactatctct gcccaaatgg aactgactgt gacagtgacc   300
agtgtgaagt tcaccgaaga gctaaaaaac cactcttccc aggaattcca ggagttcaaa   360
cagacattca cggaacagat gaatattgtg tattccggga tccctgagta tgtcggggtg   420
aacatcacaa agctacgtct tggcagtgtg gtggtggagc atgacgtcct cctaagaacc   480
aagtacacac cagaatacaa gacagtattg gacaatgcca ccgaagtagt gaaagggaaa   540
atcacaaaag tgaccacaca gcaaataatg attaatgata tttgctcaga catgatgtgt   600
ttcaacacca ctggcaccca gtgcaaaaac attacggtga cccagtacga ccctgaagag   660
gactgccgga agatggccaa ggaatatgga gactacttcg tagtggagta ccggaccag    720 aagccatact gcatcagccc ctgtgagcct ggcttcagtg tctccaagaa ctgtagcctc   780
ggcaagtgcc agatgtctct aagtggacct cagtgcctct gcgtgaccac ggaaactcac   840
tggtacagtg gggagacctg taaccagggc acccagaaga gtctggaacc tcgcggaccg   900
acaatcaagc cctgtcctcc atgcaaatgc ccagcaccta acctcttggg tggaccatcc   960
gtcttcatct tccctccaaa gatcaaggat gtactcatga tctcccctga gccccatagtc  1020 acatgtgtgg tggtggatgt gagcgaggat gacccagatg tccagatcag ctggtttgtg  1080
aacaacgtgg aagtacacac agctcagaca caaacccata gaggattaa caacagtact   1140 ctccgggtgg tcagtgccct ccccatccag caccaggact ggatgagtgg caaggagttc   1200
aaatgcaagg tcaacaacaa agacctgcca gcgcccatcg agaaccatc tcaaaaccc    1260 aaagggtcag taagagctcc acaggtatat gtcttgcctc caccagaaga agagatgact  1320
aagaaacagg tcactctgac ctgcatggtc acagacttca tgcctgaaga catttacgtg   1380
gagtggacca caacgggaaa acagagctaa aactacaaga cactgaacc agtcctggac   1440
```

```
tctgatggtt cttacttcat gtacagcaag ctgagagtgg aaaagaagaa ctgggtggaa    1500
agaaatagct actcctgttc agtggtccac gagggtctgc acaatcacca cacgactaag    1560
agcttctccc ggactccggg taaatga                                        1587
```

<210> SEQ ID NO 35
<211> LENGTH: 528
<212> TYPE: PRT
<213> ORGANISM: Artificial
<220> FEATURE:
<223> OTHER INFORMATION: Muc17 fusion protein

<400> SEQUENCE: 35

```
Met Asp Trp Thr Trp Arg Phe Leu Phe Val Val Ala Ala Ala Thr Gly
1               5                   10                  15

Val Gln Ser Thr Asn Thr Thr Ile Lys Ser Asn Pro Thr Ser Thr Pro
            20                  25                  30

Thr Val Pro Arg Thr Thr Thr Cys Phe Gly Asp Gly Cys Gln Asn Thr
        35                  40                  45

Ala Ser Arg Cys Lys Asn Gly Gly Thr Trp Asp Gly Leu Lys Cys Gln
    50                  55                  60

Cys Pro Asn Leu Tyr Tyr Gly Glu Leu Cys Glu Val Val Ser Ser
65                  70                  75                  80

Ile Asp Ile Gly Pro Pro Glu Thr Ile Ser Ala Gln Met Glu Leu Thr
                85                  90                  95

Val Thr Val Thr Ser Val Lys Phe Thr Glu Glu Leu Lys Asn His Ser
            100                 105                 110

Ser Gln Glu Phe Gln Glu Phe Lys Gln Thr Phe Thr Glu Gln Met Asn
        115                 120                 125

Ile Val Tyr Ser Gly Ile Pro Glu Tyr Val Gly Val Asn Ile Thr Lys
    130                 135                 140

Leu Arg Leu Gly Ser Val Val Glu His Asp Val Leu Leu Arg Thr
145                 150                 155                 160

Lys Tyr Thr Pro Glu Tyr Lys Thr Val Leu Asp Asn Ala Thr Glu Val
                165                 170                 175

Val Lys Gly Lys Ile Thr Lys Val Thr Thr Gln Gln Ile Met Ile Asn
            180                 185                 190

Asp Ile Cys Ser Asp Met Met Cys Phe Asn Thr Thr Gly Thr Gln Val
        195                 200                 205

Gln Asn Ile Thr Val Thr Gln Tyr Asp Pro Glu Glu Asp Cys Arg Lys
    210                 215                 220

Met Ala Lys Glu Tyr Gly Asp Tyr Phe Val Val Glu Tyr Arg Asp Gln
225                 230                 235                 240

Lys Pro Tyr Cys Ile Ser Pro Cys Glu Pro Gly Phe Ser Val Ser Lys
                245                 250                 255

Asn Cys Ser Leu Gly Lys Cys Gln Met Ser Leu Ser Gly Pro Gln Cys
            260                 265                 270

Leu Cys Val Thr Thr Glu Thr His Trp Tyr Ser Gly Glu Thr Cys Asn
        275                 280                 285

Gln Gly Thr Gln Lys Ser Leu Glu Pro Arg Gly Pro Thr Ile Lys Pro
    290                 295                 300

Cys Pro Pro Cys Lys Cys Pro Ala Pro Asn Leu Leu Gly Gly Pro Ser
305                 310                 315                 320

Val Phe Ile Phe Pro Pro Lys Ile Lys Asp Val Leu Met Ile Ser Leu
                325                 330                 335
```

```
Ser Pro Ile Val Thr Cys Val Val Asp Val Ser Glu Asp Pro
            340             345             350

Asp Val Gln Ile Ser Trp Phe Val Asn Asn Val Glu Val His Thr Ala
            355             360             365

Gln Thr Gln Thr His Arg Glu Asp Tyr Asn Ser Thr Leu Arg Val Val
    370             375             380

Ser Ala Leu Pro Ile Gln His Gln Asp Trp Met Ser Gly Lys Glu Phe
385             390             395             400

Lys Cys Lys Val Asn Asn Lys Asp Leu Pro Ala Pro Ile Glu Arg Thr
                405             410             415

Ile Ser Lys Pro Lys Gly Ser Val Arg Ala Pro Gln Val Tyr Val Leu
            420             425             430

Pro Pro Pro Glu Glu Glu Met Thr Lys Lys Gln Val Thr Leu Thr Cys
            435             440             445

Met Val Thr Asp Phe Met Pro Glu Asp Ile Tyr Val Glu Trp Thr Asn
    450             455             460

Asn Gly Lys Thr Glu Leu Asn Tyr Lys Asn Thr Glu Pro Val Leu Asp
465             470             475             480

Ser Asp Gly Ser Tyr Phe Met Tyr Ser Lys Leu Arg Val Glu Lys Lys
            485             490             495

Asn Trp Val Glu Arg Asn Ser Tyr Ser Cys Ser Val Val His Glu Gly
                500             505             510

Leu His Asn His His Thr Thr Lys Ser Phe Ser Arg Thr Pro Gly Lys
            515             520             525

<210> SEQ ID NO 36
<211> LENGTH: 21
<212> TYPE: DNA
<213> ORGANISM: Mus musculus

<400> SEQUENCE: 36
gggccagtgg atagacagat g                                              21

<210> SEQ ID NO 37
<211> LENGTH: 23
<212> TYPE: DNA
<213> ORGANISM: Mus musculus

<400> SEQUENCE: 37
gctcactgga tggtgggaag atg                                            23

<210> SEQ ID NO 38
<211> LENGTH: 16
<212> TYPE: PRT
<213> ORGANISM: homo sapiens

<400> SEQUENCE: 38

Pro Thr Thr Ala Glu Gly Thr Ser Met Pro Ser Thr Pro Ser Glu
1               5                   10                  15
```